United States Patent
Rockey et al.

(10) Patent No.: US 6,746,676 B1
(45) Date of Patent: Jun. 8, 2004

(54) CHLAMYDIA PROTEINS AND THEIR USES

(75) Inventors: Daniel D. Rockey, Corvallis, OR (US); John P. Bannantine, Ames, IA (US)

(73) Assignee: State of Oregon Acting by and Through the State Board of Higher Education on Behalf of Oregon State University, Corvallis, OR (US)

(*) Notice: Subject to any disclaimer, the term of this patent is extended or adjusted under 35 U.S.C. 154(b) by 0 days.

(21) Appl. No.: 09/673,763

(22) PCT Filed: Apr. 20, 1999

(86) PCT No.: PCT/US99/08744

§ 371 (c)(1),
(2), (4) Date: Oct. 16, 2000

(87) PCT Pub. No.: WO99/53948

PCT Pub. Date: Oct. 28, 1999

Related U.S. Application Data

(60) Provisional application No. 60/086,450, filed on May 22, 1998, provisional application No. 60/082,588, filed on Apr. 21, 1998, and provisional application No. 60/082,438, filed on Apr. 20, 1998.

(51) Int. Cl.[7] ...................... A61K 39/118; A61K 49/00; A61K 39/00

(52) U.S. Cl. ...................... 424/263.1; 424/9.1; 424/9.2; 424/184.1; 424/185.1; 424/190.1; 424/234.1; 424/278.1; 530/300; 530/350

(58) Field of Search ...................... 424/9.1, 9.2, 184.1, 424/185.1, 190.1, 234.1, 263.1, 278.1; 530/300, 350

(56) References Cited

FOREIGN PATENT DOCUMENTS

WO          WO95/11309       *  4/1995    ........... C12N/15/85

OTHER PUBLICATIONS

Rockey and Rosquist, "Protein Antigens of *Chlamydia psittaci* Present in Infected Cells but Not Detected in the Infectious Elementary Body," *Inf. Imm.*, 62:106–112, Jan. 1994.

Rockey et al., "Cloning and characterization of a *Chlamydia psittaci* gene coding for a protein localized in the inclusion membrane of infected cells," *Mol. Microbiol.*, 15:617–626, 1995.

Dyer et al., "Analysis of a cation–transporting ATPase of *Plasmodium falciparum*," *Mol. Biochem. Parasitology*, 78:1–12, 1996.

Peeling and Brunham, "Chlamydiae as Pathogens: New Species and New Issues," *Emerging Infec. Dis.*, 2:307–317, Oct.–Dec. 1996.

Rockey et al., "*Chlamydia psittaci* IncA is phosphorylated by the host cell and is exposed on the cytoplasmic face of the developing inclusion," *Mol. Microbiol.*, 24:217–228, 1997.

Hackstadt, et al., "Origins and functions of the chlamydial inclusion," *Trends Microbiol.*, 5:288–293, Jul. 1997.

Stephens et al., "Genome Sequence of an Obligate Intracellular Pathogen of Humans: *Chlamydia trachomatis*," *Science*, 282:754–759, Oct. 23, 1998.

Bannantine et al., "*Chlamydia trachomatis* IncA Is Localized to the Inclusion Membrane and Is Recognized by Antisera from Infected Humans and Primates," *Infection and Immunity*, 66:6017–6021, Dec. 1998.

Medline Accession No. AF067958, "Chlamydia trachomatis inclusion membrane protein (incA) gene, complete cds.," Dec. 03, 1998.

Medline Accession No. L35036, "Chlamydia psittaci (clones pGP12 and PGP17) inclusion membrane localised protein (incA) gene and ORF2, complete cds.," Feb. 02, 1999.

* cited by examiner

Primary Examiner—Rodney P. Swartz
(74) Attorney, Agent, or Firm—Klarquist Sparkman, LLP

(57) ABSTRACT

Certain Chlamydia proteins have been found to be infection-specific and to be associated primarily with the vegetative Reticulate Body form of Chlamydia rather than with the refractile Elementary Body form of Chlamydia. The invention includes a vaccine directed against the Reticulate Body form of Chlamydia comprising one or more infection-specific proteins, or fraction thereof; a method of using such a vaccine; a method of production of such a vaccine; a method for detection of infection-specific antibodies in a biological specimen; a method for detection of infection-specific antigens in a biological specimen and a method of using therapeutic agents specifically directed against infection-specific peptides, or the genes that code for such peptides, to treat chlamydial infection. The invention also includes the IncB, and IncC proteins of *C. psittaci*, and nucleotides encoding these proteins, ant the TroA, TroB and p242 proteins of *C. trachomatis*, and the nucleotides that encode polypeptides.

38 Claims, No Drawings

SEQUENCE LISTING

<160> NUMBER OF SEQ ID NOS: 24

<210> SEQ ID NO 1
<211> LENGTH: 534
<212> TYPE: DNA
<213> ORGANISM: Chlamydia trachomatis
<220> FEATURE:
<221> NAME/KEY: CDS
<222> LOCATION: (1)..(534)

<400> SEQUENCE: 1

```
atg aaa aag ttc tta tta ctt agc tta atg tct ttg tca tct cta cct      48
Met Lys Lys Phe Leu Leu Leu Ser Leu Met Ser Leu Ser Ser Leu Pro
 1               5                  10                  15 aca ttt gca gct aat tct aca ggc aca att gga tcg gtt aat tta cgt      96
Thr Phe Ala Ala Asn Ser Thr Gly Thr Ile Gly Ile Val Asn Leu Arg
                20                  25                  30 cgc tgc cta gaa gag tct gct ctt ggg aaa aaa gaa tct gct gaa ttc     144
Arg Cys Leu Glu Glu Ser Ala Leu Gly Lys Lys Glu Ser Ala Glu Phe
            35                  40                  45 gaa aag atg aaa aac caa ttc tct aac agc atg ggg aag atg gag gaa     192
Glu Lys Met Lys Asn Gln Phe Ser Asn Ser Met Gly Lys Met Glu Glu
         50                 55                  60 gaa ctg tct tct atc tat tcc aag ctc caa gac gac gat tac atg gaa     240
Glu Leu Ser Ser Ile Tyr Ser Lys Leu Gln Asp Asp Asp Tyr Met Glu
 65                 70                  75                  80 ggt cta tcc gag acc gca gct gcc gaa tta aga aaa aaa ttc gaa gat     288
Gly Leu Ser Glu Thr Ala Ala Ala Glu Leu Arg Lys Lys Phe Glu Asp
                85                  90                  95 cta tct gca gaa tac aac aca gct caa ggg cag tat tac caa ata tta     336
Leu Ser Ala Glu Tyr Asn Thr Ala Gln Gly Gln Tyr Tyr Gln Ile Leu
            100                 105                 110 aac caa agt aat ttc aag cgc atg caa aag att atg gaa gaa gtg aaa     384
Asn Gln Ser Asn Phe Lys Arg Met Gln Lys Ile Met Glu Glu Val Lys
        115                 120                 125 aaa gct tct gaa act gtg cgt att caa gaa ggc ttg tca gtc ctt ctt     432
Lys Ala Ser Glu Thr Val Arg Ile Gln Glu Gly Leu Ser Val Leu Leu
    130                 135                 140 aac gaa gat att gtc tta tct atc gat agt tcg gca gat aaa acc gat     480
Asn Glu Asp Ile Val Leu Ser Ile Asp Ser Ser Ala Asp Lys Thr Asp
145                 150                 155                 160 gct gtt att aaa gtt ctt gat gtt ctt ttc aaa ata att aac atg cga     528
Ala Val Ile Lys Val Leu Asp Val Leu Phe Lys Ile Ile Asn Met Arg
                165                 170                 175 agc tag                                                             534
Ser
```

<210> SEQ ID NO 2
<211> LENGTH: 177
<212> TYPE: PRT
<213> ORGANISM: Chlamydia trachomatis

<400> SEQUENCE: 2

```
Met Lys Lys Phe Leu Leu Leu Ser Leu Met Ser Leu Ser Ser Leu Pro
 1               5                  10                  15

Thr Phe Ala Ala Asn Ser Thr Gly Thr Ile Gly Ile Val Asn Leu Arg
                20                  25                  30

Arg Cys Leu Glu Glu Ser Ala Leu Gly Lys Lys Glu Ser Ala Glu Phe
            35                  40                  45
```

| | | | | | | | | | | | | |
|---|---|---|---|---|---|---|---|---|---|---|---|---|
|Glu|Lys|Met|Lys|Asn|Gln|Phe|Ser|Asn|Ser|Met|Gly|Lys|Met|Glu|Glu|
| |50| | | |55| | | |60| | | | |

Glu Leu Ser Ser Ile Tyr Ser Lys Leu Gln Asp Asp Tyr Met Glu
  65              70                  75                  80

Gly Leu Ser Glu Thr Ala Ala Glu Leu Arg Lys Lys Phe Glu Asp
                  85                  90                  95

Leu Ser Ala Glu Tyr Asn Thr Ala Gln Gly Gln Tyr Tyr Gln Ile Leu
              100                 105                 110

Asn Gln Ser Asn Phe Lys Arg Met Gln Lys Ile Met Glu Val Lys
              115                 120                 125

Lys Ala Ser Glu Thr Val Arg Ile Gln Glu Gly Leu Ser Val Leu Leu
  130                 135                 140

Asn Glu Asp Ile Val Leu Ser Ile Asp Ser Ser Ala Asp Lys Thr Asp
  145                 150                 155                 160

Ala Val Ile Lys Val Leu Asp Val Leu Phe Lys Ile Ile Asn Met Arg
                  165                 170                 175

Ser

<210> SEQ ID NO 3
<211> LENGTH: 846
<212> TYPE: DNA
<213> ORGANISM: Chlamydia trachomatis
<220> FEATURE:
<221> NAME/KEY: CDS
<222> LOCATION: (1)..(846)

<400> SEQUENCE: 3

```
atg aat cgc atg att tgt gat tgc gtg tct cgc ata act ggg gat cga      48
Met Asn Arg Met Ile Cys Asp Cys Val Ser Arg Ile Thr Gly Asp Arg
  1               5                  10                  15 gtc aag aat att gtt ctg att gat gga gcg att gat cct cat tca tat      96
Val Lys Asn Ile Val Leu Ile Asp Gly Ala Ile Asp Pro His Ser Tyr
              20                  25                  30 gag atg gtg aag ggg gat gaa gac cga atg gct atg agc cag ctg att    144
Glu Met Val Lys Gly Asp Glu Asp Arg Met Ala Met Ser Gln Leu Ile
          35                  40                  45 ttt tgc aat ggt tta ggt tta gag cat tca gct agt tta cgt aaa cat    192
Phe Cys Asn Gly Leu Gly Leu Glu His Ser Ala Ser Leu Arg Lys His
  50                  55                  60 cta gag ggt aac cca aaa gtc gtt gat tta ggt caa cgt ttg ctt aac    240
Leu Glu Gly Asn Pro Lys Val Val Asp Leu Gly Gln Arg Leu Leu Asn
 65                  70                  75                  80 aaa aac tgt ttt gat ctt ctg agt gaa gaa gga ttc cct gac cca cat    288
Lys Asn Cys Phe Asp Leu Leu Ser Glu Glu Gly Phe Pro Asp Pro His
              85                  90                  95 att tgg acg gat atg aga gta tgg ggt gct gct gta aaa gag atg gct    336
Ile Trp Thr Asp Met Arg Val Trp Gly Ala Ala Val Lys Glu Met Ala
          100                 105                 110 gcg gca tta att caa caa ttt cct caa tat gaa gaa gat ttt caa aag    384
Ala Ala Leu Ile Gln Gln Phe Pro Gln Tyr Glu Glu Asp Phe Gln Lys
      115                 120                 125 aat gcg gat cag atc tta tca gag atg gag gaa ctt gat cgt tgg gca    432
Asn Ala Asp Gln Ile Leu Ser Glu Met Glu Glu Leu Asp Arg Trp Ala
130                 135                 140 gtg cgt tct ctc tct acg att cct gaa aaa aat cgc tat tta gtc aca    480
Val Arg Ser Leu Ser Thr Ile Pro Glu Lys Asn Arg Tyr Leu Val Thr
145                 150                 155                 160 ggc cac aat gcg ttc agt tac ttt act cgt cgg tat cta tcc tct gat    528
Gly His Asn Ala Phe Ser Tyr Phe Thr Arg Arg Tyr Leu Ser Ser Asp
```

```
gcg gag aga gtg tct ggg gaa tgg aga tcg cgt tgc att tct cca gaa    576
Ala Glu Arg Val Ser Gly Glu Trp Arg Ser Arg Cys Ile Ser Pro Glu
        180                 185                 190 ggg ttg tct cct gag gct cag att agt atc cga gat att atg cgt gta    624
Gly Leu Ser Pro Glu Ala Gln Ile Ser Ile Arg Asp Ile Met Arg Val
            195                 200                 205 gtg gag tat atc tct gca aac gat gta gaa gtt gtc ttt tta gag gat    672
Val Glu Tyr Ile Ser Ala Asn Asp Val Glu Val Val Phe Leu Glu Asp
    210                 215                 220 acg tta aat caa gat gct ttg aga aag att gtt tct tgc tct aag agc    720
Thr Leu Asn Gln Asp Ala Leu Arg Lys Ile Val Ser Cys Ser Lys Ser
225                 230                 235                 240 gga caa aag att cgt ctc gct aag tct cct tta tat agc gat aat gtc    768
Gly Gln Lys Ile Arg Leu Ala Lys Ser Pro Leu Tyr Ser Asp Asn Val
                245                 250                 255 tgt gat aac tat ttt agc acg ttc cag cac aat gtt cgc aca att aca    816
Cys Asp Asn Tyr Phe Ser Thr Phe Gln His Asn Val Arg Thr Ile Thr
            260                 265                 270 gaa gaa ttg gga ggg act gtt ctt gaa tag                            846
Glu Glu Leu Gly Gly Thr Val Leu Glu
    275                 280
```

<210> SEQ ID NO 4
<211> LENGTH: 281
<212> TYPE: PRT
<213> ORGANISM: Chlamydia trachomatis

<400> SEQUENCE: 4

```
Met Asn Arg Met Ile Cys Asp Cys Val Ser Arg Ile Thr Gly Asp Arg
 1               5                  10                  15

Val Lys Asn Ile Val Leu Ile Asp Gly Ala Ile Asp Pro His Ser Tyr
                20                  25                  30

Glu Met Val Lys Gly Asp Glu Asp Arg Met Ala Met Ser Gln Leu Ile
            35                  40                  45

Phe Cys Asn Gly Leu Gly Leu Glu His Ser Ala Ser Leu Arg Lys His
        50                  55                  60

Leu Glu Gly Asn Pro Lys Val Val Asp Leu Gly Gln Arg Leu Leu Asn
65                  70                  75                  80

Lys Asn Cys Phe Asp Leu Leu Ser Glu Glu Gly Phe Pro Asp Pro His
                85                  90                  95

Ile Trp Thr Asp Met Arg Val Trp Gly Ala Ala Val Lys Glu Met Ala
            100                 105                 110

Ala Ala Leu Ile Gln Gln Phe Pro Gln Tyr Glu Glu Asp Phe Gln Lys
        115                 120                 125

Asn Ala Asp Gln Ile Leu Ser Glu Met Glu Glu Leu Asp Arg Trp Ala
    130                 135                 140

Val Arg Ser Leu Ser Thr Ile Pro Glu Lys Asn Arg Tyr Leu Val Thr
145                 150                 155                 160

Gly His Asn Ala Phe Ser Tyr Phe Thr Arg Arg Tyr Leu Ser Ser Asp
                165                 170                 175

Ala Glu Arg Val Ser Gly Glu Trp Arg Ser Arg Cys Ile Ser Pro Glu
            180                 185                 190

Gly Leu Ser Pro Glu Ala Gln Ile Ser Ile Arg Asp Ile Met Arg Val
        195                 200                 205

Val Glu Tyr Ile Ser Ala Asn Asp Val Glu Val Val Phe Leu Glu Asp
    210                 215                 220
```

```
Thr Leu Asn Gln Asp Ala Leu Arg Lys Ile Val Ser Cys Ser Lys Ser
225                 230                 235                 240

Gly Gln Lys Ile Arg Leu Ala Lys Ser Pro Leu Tyr Ser Asp Asn Val
            245                 250                 255

Cys Asp Asn Tyr Phe Ser Thr Phe Gln His Asn Val Arg Thr Ile Thr
                260                 265                 270

Glu Glu Leu Gly Gly Thr Val Leu Glu
            275                 280

<210> SEQ ID NO 5
<211> LENGTH: 861
<212> TYPE: DNA
<213> ORGANISM: Chlamydia trachomatis
<220> FEATURE:
<221> NAME/KEY: CDS
<222> LOCATION: (1)..(861)

<400> SEQUENCE: 5 atg tct gtg ata act att tta gca cgt tcc agc aca atg ttc gca caa      48
Met Ser Val Ile Thr Ile Leu Ala Arg Ser Ser Thr Met Phe Ala Gln
  1               5                  10                  15 tta cag aag aat tgg gag gga ctg ttc ttg aat aga gat aat gca att      96
Leu Gln Lys Asn Trp Glu Gly Leu Phe Leu Asn Arg Asp Asn Ala Ile
             20                  25                  30 gct tgg tcc gta gag gat ctt tgt gtt aat tat gat cac tca gac gtc     144
Ala Trp Ser Val Glu Asp Leu Cys Val Asn Tyr Asp His Ser Asp Val
         35                  40                  45 tta tgt cac att act ttt tct ctg cct gca ggg gca atg gct gct att     192
Leu Cys His Ile Thr Phe Ser Leu Pro Ala Gly Ala Met Ala Ala Ile
     50                  55                  60 att ggg ccg aat gga gct ggt aaa agt act ttg ctt aag gct tct tta     240
Ile Gly Pro Asn Gly Ala Gly Lys Ser Thr Leu Leu Lys Ala Ser Leu
 65                  70                  75                  80 gga ctg att cgt gct tct tct ggc caa agc ttg ttc ttt ggt cag aga     288
Gly Leu Ile Arg Ala Ser Ser Gly Gln Ser Leu Phe Phe Gly Gln Arg
                 85                  90                  95 ttt tcc aag gca cat cat aga ata gcc tat atg cct caa aga gcg agt     336
Phe Ser Lys Ala His His Arg Ile Ala Tyr Met Pro Gln Arg Ala Ser
            100                 105                 110 gtg gat tgg gat ttc cca atg act gtt ctt gat ctc gtg ttg atg ggg     384
Val Asp Trp Asp Phe Pro Met Thr Val Leu Asp Leu Val Leu Met Gly
        115                 120                 125 tgt tac ggc tat aaa gga ata tgg aat cgt att tcc act gat gat cgt     432
Cys Tyr Gly Tyr Lys Gly Ile Trp Asn Arg Ile Ser Thr Asp Asp Arg
    130                 135                 140 cag gag gct atg cgt att tta gag cgg gtt ggt ttg gaa gct ttt gca     480
Gln Glu Ala Met Arg Ile Leu Glu Arg Val Gly Leu Glu Ala Phe Ala
145                 150                 155                 160 aat cgt caa ata ggt aag ctc tct gga gga caa caa cag aga gct ttt     528
Asn Arg Gln Ile Gly Lys Leu Ser Gly Gly Gln Gln Gln Arg Ala Phe
                165                 170                 175 tta gcg cgg tca tta atg caa aaa gca gat ttg tat ctc atg gat gag     576
Leu Ala Arg Ser Leu Met Gln Lys Ala Asp Leu Tyr Leu Met Asp Glu
            180                 185                 190 ctg ttc tct gcg atc gat atg gcc tct tat cag atg gtt gta gat gtt     624
Leu Phe Ser Ala Ile Asp Met Ala Ser Tyr Gln Met Val Val Asp Val
        195                 200                 205 ttg caa gag ctt aaa agc gaa ggg aag act att gtg gtc att cat cat     672
Leu Gln Glu Leu Lys Ser Glu Gly Lys Thr Ile Val Val Ile His His
    210                 215                 220
```

```
gat ttg agt aat gtc cgg aag ctt ttt gat cat gtg att tta tta aat    720
Asp Leu Ser Asn Val Arg Lys Leu Phe Asp His Val Ile Leu Leu Asn
225                 230                 235                 240 aag cat ctt gtg tgc tct gga agc gta gaa gaa tgc ttg act aaa gaa    768
Lys His Leu Val Cys Ser Gly Ser Val Glu Glu Cys Leu Thr Lys Glu
                245                 250                 255 gcc att ttt cag gct tat ggg tgt gac ttg agc ttt tgg att aca cac    816
Ala Ile Phe Gln Ala Tyr Gly Cys Asp Leu Ser Phe Trp Ile Thr His
            260                 265                 270 tca aat tgt cta gag gca agt acc aag gat cgt gct aga tgc tga        861
Ser Asn Cys Leu Glu Ala Ser Thr Lys Asp Arg Ala Arg Cys
        275                 280                 285
```

<210> SEQ ID NO 6
<211> LENGTH: 286
<212> TYPE: PRT
<213> ORGANISM: Chlamydia trachomatis

<400> SEQUENCE: 6

```
Met Ser Val Ile Thr Ile Leu Ala Arg Ser Ser Thr Met Phe Ala Gln
  1               5                  10                  15

Leu Gln Lys Asn Trp Glu Gly Leu Phe Leu Asn Arg Asp Asn Ala Ile
             20                  25                  30

Ala Trp Ser Val Glu Asp Leu Cys Val Asn Tyr Asp His Ser Asp Val
         35                  40                  45

Leu Cys His Ile Thr Phe Ser Leu Pro Ala Gly Ala Met Ala Ala Ile
     50                  55                  60

Ile Gly Pro Asn Gly Ala Gly Lys Ser Thr Leu Leu Lys Ala Ser Leu
 65                  70                  75                  80

Gly Leu Ile Arg Ala Ser Ser Gly Gln Ser Leu Phe Phe Gly Gln Arg
                 85                  90                  95

Phe Ser Lys Ala His His Arg Ile Ala Tyr Met Pro Gln Arg Ala Ser
                100                 105                 110

Val Asp Trp Asp Phe Pro Met Thr Val Leu Asp Leu Val Leu Met Gly
            115                 120                 125

Cys Tyr Gly Tyr Lys Gly Ile Trp Asn Arg Ile Ser Thr Asp Asp Arg
        130                 135                 140

Gln Glu Ala Met Arg Ile Leu Glu Arg Val Gly Leu Glu Ala Phe Ala
145                 150                 155                 160

Asn Arg Gln Ile Gly Lys Leu Ser Gly Gly Gln Gln Arg Ala Phe
                165                 170                 175

Leu Ala Arg Ser Leu Met Gln Lys Ala Asp Leu Tyr Leu Met Asp Glu
            180                 185                 190

Leu Phe Ser Ala Ile Asp Met Ala Ser Tyr Gln Met Val Val Asp Val
        195                 200                 205

Leu Gln Glu Leu Lys Ser Glu Gly Lys Thr Ile Val Val Ile His His
    210                 215                 220

Asp Leu Ser Asn Val Arg Lys Leu Phe Asp His Val Ile Leu Leu Asn
225                 230                 235                 240

Lys His Leu Val Cys Ser Gly Ser Val Glu Glu Cys Leu Thr Lys Glu
                245                 250                 255

Ala Ile Phe Gln Ala Tyr Gly Cys Asp Leu Ser Phe Trp Ile Thr His
            260                 265                 270

Ser Asn Cys Leu Glu Ala Ser Thr Lys Asp Arg Ala Arg Cys
        275                 280                 285
```

-continued

```
<210> SEQ ID NO 7
<211> LENGTH: 1068
<212> TYPE: DNA
<213> ORGANISM: Chlamydia psittaci
<220> FEATURE:
<221> NAME/KEY: CDS
<222> LOCATION: (1)..(1068)

<400> SEQUENCE: 7 atg aca gta tcc aca gac aac aca agt cct gta ata tcg aga gcg tcc       48
Met Thr Val Ser Thr Asp Asn Thr Ser Pro Val Ile Ser Arg Ala Ser
  1               5                  10                  15 tca cct act ttt gga gat cat ggt aag gat ttc gac aac aat aaa att       96
Ser Pro Thr Phe Gly Asp His Gly Lys Asp Phe Asp Asn Asn Lys Ile
             20                  25                  30 ata ccc att tca ata gaa gct cca act tct tca gct gct gct gta ggg      144
Ile Pro Ile Ser Ile Glu Ala Pro Thr Ser Ser Ala Ala Ala Val Gly
         35                  40                  45 gct aaa acg gct atc gag cct gaa gga aga agc cca cta ctt caa agg      192
Ala Lys Thr Ala Ile Glu Pro Glu Gly Arg Ser Pro Leu Leu Gln Arg
     50                  55                  60 att tgc tat ctt gtt aaa att atc gct gcc atc gcc ctc ttt gtt gtt      240
Ile Cys Tyr Leu Val Lys Ile Ile Ala Ala Ile Ala Leu Phe Val Val
 65                  70                  75                  80 ggt atc gca gcc tta gtt tgc tta tat ctc ggt agc gtt atc tca acg      288
Gly Ile Ala Ala Leu Val Cys Leu Tyr Leu Gly Ser Val Ile Ser Thr
                 85                  90                  95 cct tct ctt att ctt atg ctt gcg atc atg ctt gta tcc ttt gtg atc      336
Pro Ser Leu Ile Leu Met Leu Ala Ile Met Leu Val Ser Phe Val Ile
            100                 105                 110 gtt att acg gca att cga gat ggc aca ccg tct caa gtg gtc cgt cac      384
Val Ile Thr Ala Ile Arg Asp Gly Thr Pro Ser Gln Val Val Arg His
        115                 120                 125 atg aaa cag caa att cag caa ttt ggc gaa gaa aac acg cgt tta cat      432
Met Lys Gln Gln Ile Gln Gln Phe Gly Glu Glu Asn Thr Arg Leu His
    130                 135                 140 acc gca gta gaa aat cta aaa gct gtt aac gtt gag ctc tca gag caa      480
Thr Ala Val Glu Asn Leu Lys Ala Val Asn Val Glu Leu Ser Glu Gln
145                 150                 155                 160 att aac caa ctt aaa caa cta cat act aga tta tcg gat ttt ggt gat      528
Ile Asn Gln Leu Lys Gln Leu His Thr Arg Leu Ser Asp Phe Gly Asp
                165                 170                 175 agg ctt gaa gcg aat acc ggt gat ttt act gca ctt att gcg gat ttc      576
Arg Leu Glu Ala Asn Thr Gly Asp Phe Thr Ala Leu Ile Ala Asp Phe
            180                 185                 190 caa ctc agt ctg gaa gag ttt aag tct gtt ggt act aaa gtt gaa acc      624
Gln Leu Ser Leu Glu Glu Phe Lys Ser Val Gly Thr Lys Val Glu Thr
        195                 200                 205 atg ctc tct cca ttt gag aaa tta gct cag tct ttg aaa gag acc ttt      672
Met Leu Ser Pro Phe Glu Lys Leu Ala Gln Ser Leu Lys Glu Thr Phe
    210                 215                 220 tct caa gaa gct gtt cag gca atg atg tcc tct gta act gag tta aga      720
Ser Gln Glu Ala Val Gln Ala Met Met Ser Ser Val Thr Glu Leu Arg
225                 230                 235                 240 acc aat ttg aat gca ttg aaa gag ctt ata aca gag aat aaa acc gta      768
Thr Asn Leu Asn Ala Leu Lys Glu Leu Ile Thr Glu Asn Lys Thr Val
                245                 250                 255 ata gag caa cta aaa gct gat gct caa ctt aga gaa gag caa gtg cgg      816
Ile Glu Gln Leu Lys Ala Asp Ala Gln Leu Arg Glu Glu Gln Val Arg
            260                 265                 270
```

```
ttt tta gaa aag cgt aaa caa gag tta gaa gag gct tgt tca aca ttg      864
Phe Leu Glu Lys Arg Lys Gln Glu Leu Glu Glu Ala Cys Ser Thr Leu
            275                 280                 285 tcc cat tca att gcg act cta cag gaa tcc aca acc ctt cta aag gac      912
Ser His Ser Ile Ala Thr Leu Gln Glu Ser Thr Thr Leu Leu Lys Asp
        290                 295                 300 tct aca act aac tta cat gca gtt gaa agt cgt ctt atc ggt gtt atg      960
Ser Thr Thr Asn Leu His Ala Val Glu Ser Arg Leu Ile Gly Val Met
305                 310                 315                 320 gtt cag gat ggt gca gag tcc tcc acc gta gag gaa gct tca caa gat     1008
Val Gln Asp Gly Ala Glu Ser Ser Thr Val Glu Glu Ala Ser Gln Asp
                325                 330                 335 gat agc gcg caa ccc caa gat gaa aat caa tct gat gct gga gag cat     1056
Asp Ser Ala Gln Pro Gln Asp Glu Asn Gln Ser Asp Ala Gly Glu His
            340                 345                 350 aaa gat agt taa                                                     1068
Lys Asp Ser
        355

<210> SEQ ID NO 8
<211> LENGTH: 355
<212> TYPE: PRT
<213> ORGANISM: Chlamydia psittaci

<400> SEQUENCE: 8

Met Thr Val Ser Thr Asp Asn Thr Ser Pro Val Ile Ser Arg Ala Ser
  1               5                  10                  15

Ser Pro Thr Phe Gly Asp His Gly Lys Asp Phe Asp Asn Asn Lys Ile
             20                  25                  30

Ile Pro Ile Ser Ile Glu Ala Pro Thr Ser Ser Ala Ala Ala Val Gly
         35                  40                  45

Ala Lys Thr Ala Ile Glu Pro Glu Gly Arg Ser Pro Leu Leu Gln Arg
     50                  55                  60

Ile Cys Tyr Leu Val Lys Ile Ala Ala Ile Ala Leu Phe Val Val
 65                  70                  75                  80

Gly Ile Ala Ala Leu Val Cys Leu Tyr Leu Gly Ser Val Ile Ser Thr
                 85                  90                  95

Pro Ser Leu Ile Leu Met Leu Ala Ile Met Leu Val Ser Phe Val Ile
            100                 105                 110

Val Ile Thr Ala Ile Arg Asp Gly Thr Pro Ser Gln Val Val Arg His
        115                 120                 125

Met Lys Gln Gln Ile Gln Gln Phe Gly Glu Glu Asn Thr Arg Leu His
    130                 135                 140

Thr Ala Val Glu Asn Leu Lys Ala Val Asn Val Glu Leu Ser Glu Gln
145                 150                 155                 160

Ile Asn Gln Leu Lys Gln Leu His Thr Arg Leu Ser Asp Phe Gly Asp
                165                 170                 175

Arg Leu Glu Ala Asn Thr Gly Asp Phe Thr Ala Leu Ile Ala Asp Phe
            180                 185                 190

Gln Leu Ser Leu Glu Glu Phe Lys Ser Val Gly Thr Lys Val Glu Thr
        195                 200                 205

Met Leu Ser Pro Phe Glu Lys Leu Ala Gln Ser Leu Lys Glu Thr Phe
    210                 215                 220

Ser Gln Glu Ala Val Gln Ala Met Met Ser Ser Val Thr Glu Leu Arg
225                 230                 235                 240

Thr Asn Leu Asn Ala Leu Lys Glu Leu Ile Thr Glu Asn Lys Thr Val
                245                 250                 255
```

-continued

```
Ile Glu Gln Leu Lys Ala Asp Ala Gln Leu Arg Glu Glu Gln Val Arg
            260                 265                 270

Phe Leu Glu Lys Arg Lys Gln Glu Leu Glu Glu Ala Cys Ser Thr Leu
        275                 280                 285

Ser His Ser Ile Ala Thr Leu Gln Glu Ser Thr Thr Leu Leu Lys Asp
    290                 295                 300

Ser Thr Thr Asn Leu His Ala Val Glu Ser Arg Leu Ile Gly Val Met
305                 310                 315                 320

Val Gln Asp Gly Ala Glu Ser Ser Thr Val Glu Glu Ala Ser Gln Asp
                325                 330                 335

Asp Ser Ala Gln Pro Gln Asp Glu Asn Gln Ser Asp Ala Gly Glu His
            340                 345                 350

Lys Asp Ser
        355

<210> SEQ ID NO 9
<211> LENGTH: 597
<212> TYPE: DNA
<213> ORGANISM: Chlamydia psittaci
<220> FEATURE:
<221> NAME/KEY: CDS
<222> LOCATION: (1)..(597)

<400> SEQUENCE: 9 atg tca aca aca cca gca tct tca gca agt cga gac gta tta tta gat       48
Met Ser Thr Thr Pro Ala Ser Ser Ala Ser Arg Asp Val Leu Leu Asp
  1               5                  10                  15 gac gtt tta ata gct ttt aat aga aag cta aat ctc gta gaa caa caa       96
Asp Val Leu Ile Ala Phe Asn Arg Lys Leu Asn Leu Val Glu Gln Gln
            20                  25                  30 gcg aaa gaa ctt gaa acg aaa gtc agt ttg gta gac aga aca gct act      144
Ala Lys Glu Leu Glu Thr Lys Val Ser Leu Val Asp Arg Thr Ala Thr
        35                  40                  45 tta tca ctt acc act ggc aat aat gta gcc acg gat gta ctc ctt tta      192
Leu Ser Leu Thr Thr Gly Asn Asn Val Ala Thr Asp Val Leu Leu Leu
    50                  55                  60 aaa gat gag gtt gca gaa cta aaa gga tgt ttg tct gca gtt acg gat      240
Lys Asp Glu Val Ala Glu Leu Lys Gly Cys Leu Ser Ala Val Thr Asp
 65                  70                  75                  80 cta tta atc cgc tca ggc tca tca aga aca cct ggg ggt gct cct aat      288
Leu Leu Ile Arg Ser Gly Ser Ser Arg Thr Pro Gly Gly Ala Pro Asn
                85                  90                  95 cca gaa ggc act aat tac cta ata gga tgc aca cct cct tct ctt tgc      336
Pro Glu Gly Thr Asn Tyr Leu Ile Gly Cys Thr Pro Pro Ser Leu Cys
            100                 105                 110 gct aaa ctt aca gcg tta gcg tta aca att ata gcc ctc att gct atc      384
Ala Lys Leu Thr Ala Leu Ala Leu Thr Ile Ile Ala Leu Ile Ala Ile
        115                 120                 125 aca gta ctt gtt atc tgt att gtt act gtt tgc ggc ggt ttc ccc cta      432
Thr Val Leu Val Ile Cys Ile Val Thr Val Cys Gly Gly Phe Pro Leu
    130                 135                 140 ttt att tcc cta ctc aac atg tac aca gtt ggt gct tgt ata tcc tta      480
Phe Ile Ser Leu Leu Asn Met Tyr Thr Val Gly Ala Cys Ile Ser Leu
145                 150                 155                 160 ccg atc att tcg tgt gcc gca gtt tca atg atg att cta tgc tca cat      528
Pro Ile Ile Ser Cys Ala Ala Val Ser Met Met Ile Leu Cys Ser His
                165                 170                 175 tct att aac tct tta tta aga aac agg cct gcg atc tat atg act aac      576
Ser Ile Asn Ser Leu Leu Arg Asn Arg Pro Ala Ile Tyr Met Thr Asn
```

-continued

```
            180                 185                 190 aat ttt caa aca gaa tct taa                                         597
Asn Phe Gln Thr Glu Ser
        195

<210> SEQ ID NO 10
<211> LENGTH: 198
<212> TYPE: PRT
<213> ORGANISM: Chlamydia psittaci
<400> SEQUENCE: 10

Met Ser Thr Thr Pro Ala Ser Ser Ala Ser Arg Asp Val Leu Leu Asp
  1               5                  10                  15

Asp Val Leu Ile Ala Phe Asn Arg Lys Leu Asn Leu Val Glu Gln Gln
             20                  25                  30

Ala Lys Glu Leu Glu Thr Lys Val Ser Leu Val Asp Arg Thr Ala Thr
         35                  40                  45

Leu Ser Leu Thr Thr Gly Asn Asn Val Ala Thr Asp Val Leu Leu Leu
     50                  55                  60

Lys Asp Glu Val Ala Glu Leu Lys Gly Cys Leu Ser Ala Val Thr Asp
 65                  70                  75                  80

Leu Leu Ile Arg Ser Gly Ser Ser Arg Thr Pro Gly Gly Ala Pro Asn
                 85                  90                  95

Pro Glu Gly Thr Asn Tyr Leu Ile Gly Cys Thr Pro Pro Ser Leu Cys
            100                 105                 110

Ala Lys Leu Thr Ala Leu Ala Leu Thr Ile Ile Ala Leu Ile Ala Ile
        115                 120                 125

Thr Val Leu Val Ile Cys Ile Val Thr Val Cys Gly Gly Phe Pro Leu
    130                 135                 140

Phe Ile Ser Leu Leu Asn Met Tyr Thr Val Gly Ala Cys Ile Ser Leu
145                 150                 155                 160

Pro Ile Ile Ser Cys Ala Ala Val Ser Met Met Ile Leu Cys Ser His
                165                 170                 175

Ser Ile Asn Ser Leu Leu Arg Asn Arg Pro Ala Ile Tyr Met Thr Asn
            180                 185                 190

Asn Phe Gln Thr Glu Ser
        195

<210> SEQ ID NO 11
<211> LENGTH: 561
<212> TYPE: DNA
<213> ORGANISM: Chlamydia psittaci
<220> FEATURE:
<221> NAME/KEY: CDS
<222> LOCATION: (1)..(561)

<400> SEQUENCE: 11 atg acc tct gta aga acc gat tta act cca ggc gac acc tca ctc caa       48
Met Thr Ser Val Arg Thr Asp Leu Thr Pro Gly Asp Thr Ser Leu Gln
  1               5                  10                  15 tct tct tta tta aat ccg agt gat ctc aca aca caa cta tcc aac ctc       96
Ser Ser Leu Leu Asn Pro Ser Asp Leu Thr Thr Gln Leu Ser Asn Leu
             20                  25                  30 cag act gtt ctc gca ggg ata caa caa caa cat cct tta aac ggt ggt      144
Gln Thr Val Leu Ala Gly Ile Gln Gln Gln His Pro Leu Asn Gly Gly
         35                  40                  45 tgg cct cag cat cat cct act ggc gct gca gat caa aat tat ctc atg      192
Trp Pro Gln His His Pro Thr Gly Ala Ala Asp Gln Asn Tyr Leu Met
     50                  55                  60
```

```
cgt ctg atg caa tct cat atg gca agt acc gta tca gca gta tct gaa      240
Arg Leu Met Gln Ser His Met Ala Ser Thr Val Ser Ala Val Ser Glu
 65                  70                  75                  80 tta aga acc gaa gtc act gca atc aag aca aaa ttg cac ggg cta tct      288
Leu Arg Thr Glu Val Thr Ala Ile Lys Thr Lys Leu His Gly Leu Ser
                 85                  90                  95 act cca gct aat gtt tgc agc ggt cct atg gct cta gcc gct ttt ctt      336
Thr Pro Ala Asn Val Cys Ser Gly Pro Met Ala Leu Ala Ala Phe Leu
            100                 105                 110 cta gct ata tct tta gtt gcg att atc atc att gtt tta gcc tcc tta      384
Leu Ala Ile Ser Leu Val Ala Ile Ile Ile Ile Val Leu Ala Ser Leu
        115                 120                 125 ggc ctt gca ggc ata cta cct caa gct gcc gct atc tta gtg aat aca      432
Gly Leu Ala Gly Ile Leu Pro Gln Ala Ala Ala Ile Leu Val Asn Thr
    130                 135                 140 gca aac tct ata tgg gct att gtt agc gct tcg ata gtc act gtt atc      480
Ala Asn Ser Ile Trp Ala Ile Val Ser Ala Ser Ile Val Thr Val Ile
145                 150                 155                 160 tgc tta att agc gtg cta tgc ata acg cta att cga cac cat aaa ccc      528
Cys Leu Ile Ser Val Leu Cys Ile Thr Leu Ile Arg His His Lys Pro
                165                 170                 175 tta cct att gaa act agg cct acc gga cat taa                          561
Leu Pro Ile Glu Thr Arg Pro Thr Gly His
                180                 185

<210> SEQ ID NO 12
<211> LENGTH: 186
<212> TYPE: PRT
<213> ORGANISM: Chlamydia psittaci

<400> SEQUENCE: 12

Met Thr Ser Val Arg Thr Asp Leu Thr Pro Gly Asp Thr Ser Leu Gln
  1               5                  10                  15

Ser Ser Leu Leu Asn Pro Ser Asp Leu Thr Thr Gln Leu Ser Asn Leu
                 20                  25                  30

Gln Thr Val Leu Ala Gly Ile Gln Gln His Pro Leu Asn Gly Gly
             35                  40                  45

Trp Pro Gln His His Pro Thr Gly Ala Ala Asp Gln Asn Tyr Leu Met
     50                  55                  60

Arg Leu Met Gln Ser His Met Ala Ser Thr Val Ser Ala Val Ser Glu
 65                  70                  75                  80

Leu Arg Thr Glu Val Thr Ala Ile Lys Thr Lys Leu His Gly Leu Ser
                 85                  90                  95

Thr Pro Ala Asn Val Cys Ser Gly Pro Met Ala Leu Ala Ala Phe Leu
            100                 105                 110

Leu Ala Ile Ser Leu Val Ala Ile Ile Ile Ile Val Leu Ala Ser Leu
        115                 120                 125

Gly Leu Ala Gly Ile Leu Pro Gln Ala Ala Ala Ile Leu Val Asn Thr
    130                 135                 140

Ala Asn Ser Ile Trp Ala Ile Val Ser Ala Ser Ile Val Thr Val Ile
145                 150                 155                 160

Cys Leu Ile Ser Val Leu Cys Ile Thr Leu Ile Arg His His Lys Pro
                165                 170                 175

Leu Pro Ile Glu Thr Arg Pro Thr Gly His
                180                 185

<210> SEQ ID NO 13
```

<211> LENGTH: 822
<212> TYPE: DNA
<213> ORGANISM: Chlamydia trachomatis
<220> FEATURE:
<221> NAME/KEY: CDS
<222> LOCATION: (1)..(822)

<400> SEQUENCE: 13

| | | | | | | | | | | | | | | | | |
|---|---|---|---|---|---|---|---|---|---|---|---|---|---|---|---|---|
| atg | aca | acg | cct | act | cta | atc | gtg | att | cct | cca | tct | ccc | cct | gca | cct | 48 |
| Met | Thr | Thr | Pro | Thr | Leu | Ile | Val | Ile | Pro | Pro | Ser | Pro | Pro | Ala | Pro | |
| 1 | | | | 5 | | | | | 10 | | | | | 15 | | |
| tcc | tac | tca | gcc | aat | cgc | gta | cct | caa | cct | tct | ttg | atg | gac | aaa | att | 96 |
| Ser | Tyr | Ser | Ala | Asn | Arg | Val | Pro | Gln | Pro | Ser | Leu | Met | Asp | Lys | Ile | |
| | | | 20 | | | | | 25 | | | | | 30 | | | |
| aag | aaa | ata | gca | gcc | att | gcc | tcc | cta | att | ctt | ata | ggc | aca | ata | ggc | 144 |
| Lys | Lys | Ile | Ala | Ala | Ile | Ala | Ser | Leu | Ile | Leu | Ile | Gly | Thr | Ile | Gly | |
| | | 35 | | | | | 40 | | | | | 45 | | | | |
| ttt | tta | gct | ctt | ttg | gga | cat | ctt | gtt | ggc | ttt | ctg | atc | gct | cca | caa | 192 |
| Phe | Leu | Ala | Leu | Leu | Gly | His | Leu | Val | Gly | Phe | Leu | Ile | Ala | Pro | Gln | |
| | 50 | | | | | 55 | | | | | 60 | | | | | |
| atc | act | att | gtt | ctt | ctt | gcc | cta | ttc | att | acc | tca | tta | gca | ggg | aat | 240 |
| Ile | Thr | Ile | Val | Leu | Leu | Ala | Leu | Phe | Ile | Thr | Ser | Leu | Ala | Gly | Asn | |
| 65 | | | | | 70 | | | | | 75 | | | | | 80 | |
| gct | ctt | tat | cta | cag | aaa | acc | gct | aat | cta | cat | cta | tac | cag | gat | ctg | 288 |
| Ala | Leu | Tyr | Leu | Gln | Lys | Thr | Ala | Asn | Leu | His | Leu | Tyr | Gln | Asp | Leu | |
| | | | | 85 | | | | | 90 | | | | | 95 | | |
| caa | aga | gaa | gtt | ggg | tct | cta | aaa | gaa | att | aat | ttc | atg | ctg | agc | gtt | 336 |
| Gln | Arg | Glu | Val | Gly | Ser | Leu | Lys | Glu | Ile | Asn | Phe | Met | Leu | Ser | Val | |
| | | | 100 | | | | | 105 | | | | | 110 | | | |
| cta | cag | aaa | gaa | ttt | ctt | cat | tta | tct | aaa | gaa | ttt | gca | acg | aca | tct | 384 |
| Leu | Gln | Lys | Glu | Phe | Leu | His | Leu | Ser | Lys | Glu | Phe | Ala | Thr | Thr | Ser | |
| | | 115 | | | | | 120 | | | | | 125 | | | | |
| aaa | gac | ctc | tct | gct | gta | tct | caa | gat | ttt | tat | tct | tgt | ttg | caa | gga | 432 |
| Lys | Asp | Leu | Ser | Ala | Val | Ser | Gln | Asp | Phe | Tyr | Ser | Cys | Leu | Gln | Gly | |
| | 130 | | | | | 135 | | | | | 140 | | | | | |
| ttt | aga | gat | aac | tat | aaa | ggt | ttt | gaa | tct | ctt | ttg | gat | gag | tat | aaa | 480 |
| Phe | Arg | Asp | Asn | Tyr | Lys | Gly | Phe | Glu | Ser | Leu | Leu | Asp | Glu | Tyr | Lys | |
| 145 | | | | | 150 | | | | | 155 | | | | | 160 | |
| aac | tct | aca | gaa | gaa | atg | cgc | aaa | ctc | ttt | tcg | caa | gaa | atc | ata | gca | 528 |
| Asn | Ser | Thr | Glu | Glu | Met | Arg | Lys | Leu | Phe | Ser | Gln | Glu | Ile | Ile | Ala | |
| | | | | 165 | | | | | 170 | | | | | 175 | | |
| gat | ctt | aaa | ggc | tct | gtt | gcc | tca | tta | aga | gag | gaa | atc | cga | ttc | cta | 576 |
| Asp | Leu | Lys | Gly | Ser | Val | Ala | Ser | Leu | Arg | Glu | Glu | Ile | Arg | Phe | Leu | |
| | | | 180 | | | | | 185 | | | | | 190 | | | |
| acc | cca | tta | gca | gaa | gaa | gtt | cgc | cga | tta | gcg | cat | aac | cag | gaa | tca | 624 |
| Thr | Pro | Leu | Ala | Glu | Glu | Val | Arg | Arg | Leu | Ala | His | Asn | Gln | Glu | Ser | |
| | | 195 | | | | | 200 | | | | | 205 | | | | |
| tta | aca | gcg | gct | att | gaa | gaa | tta | aaa | aca | att | cgt | gat | agc | tta | cga | 672 |
| Leu | Thr | Ala | Ala | Ile | Glu | Glu | Leu | Lys | Thr | Ile | Arg | Asp | Ser | Leu | Arg | |
| | 210 | | | | | 215 | | | | | 220 | | | | | |
| gat | gaa | att | gga | caa | ctt | tca | caa | ctt | tct | aaa | act | ctt | acc | agt | caa | 720 |
| Asp | Glu | Ile | Gly | Gln | Leu | Ser | Gln | Leu | Ser | Lys | Thr | Leu | Thr | Ser | Gln | |
| 225 | | | | | 230 | | | | | 235 | | | | | 240 | |
| att | gca | tta | caa | cga | aaa | gag | agc | tca | gat | ctg | tgt | tcc | cag | ata | aga | 768 |
| Ile | Ala | Leu | Gln | Arg | Lys | Glu | Ser | Ser | Asp | Leu | Cys | Ser | Gln | Ile | Arg | |
| | | | | 245 | | | | | 250 | | | | | 255 | | |
| gag | acg | ctc | tcc | tcc | ccc | aga | aag | tct | gca | tca | ccc | tct | aca | aaa | agc | 816 |
| Glu | Thr | Leu | Ser | Ser | Pro | Arg | Lys | Ser | Ala | Ser | Pro | Ser | Thr | Lys | Ser | |
| | | | 260 | | | | | 265 | | | | | 270 | | | |
| tcc | tag | | | | | | | | | | | | | | | 822 |
| Ser | | | | | | | | | | | | | | | | |

<210> SEQ ID NO 14
<211> LENGTH: 273
<212> TYPE: PRT
<213> ORGANISM: Chlamydia trachomatis

<400> SEQUENCE: 14

Met Thr Thr Pro Thr Leu Ile Val Ile Pro Pro Ser Pro Pro Ala Pro
 1               5                  10                  15

Ser Tyr Ser Ala Asn Arg Val Pro Gln Pro Ser Leu Met Asp Lys Ile
            20                  25                  30

Lys Lys Ile Ala Ala Ile Ala Ser Leu Ile Leu Ile Gly Thr Ile Gly
        35                  40                  45

Phe Leu Ala Leu Leu Gly His Leu Val Gly Phe Leu Ile Ala Pro Gln
    50                  55                  60

Ile Thr Ile Val Leu Leu Ala Leu Phe Ile Thr Ser Leu Ala Gly Asn
65                  70                  75                  80

Ala Leu Tyr Leu Gln Lys Thr Ala Asn Leu His Leu Tyr Gln Asp Leu
                85                  90                  95

Gln Arg Glu Val Gly Ser Leu Lys Glu Ile Asn Phe Met Leu Ser Val
            100                 105                 110

Leu Gln Lys Glu Phe Leu His Leu Ser Lys Glu Phe Ala Thr Thr Ser
        115                 120                 125

Lys Asp Leu Ser Ala Val Ser Gln Asp Phe Tyr Ser Cys Leu Gln Gly
    130                 135                 140

Phe Arg Asp Asn Tyr Lys Gly Phe Glu Ser Leu Leu Asp Glu Tyr Lys
145                 150                 155                 160

Asn Ser Thr Glu Glu Met Arg Lys Leu Phe Ser Gln Glu Ile Ile Ala
                165                 170                 175

Asp Leu Lys Gly Ser Val Ala Ser Leu Arg Glu Glu Ile Arg Phe Leu
            180                 185                 190

Thr Pro Leu Ala Glu Glu Val Arg Arg Leu Ala His Asn Gln Glu Ser
        195                 200                 205

Leu Thr Ala Ala Ile Glu Glu Leu Lys Thr Ile Arg Asp Ser Leu Arg
    210                 215                 220

Asp Glu Ile Gly Gln Leu Ser Gln Leu Ser Lys Thr Leu Thr Ser Gln
225                 230                 235                 240

Ile Ala Leu Gln Arg Lys Glu Ser Ser Asp Leu Cys Ser Gln Ile Arg
                245                 250                 255

Glu Thr Leu Ser Ser Pro Arg Lys Ser Ala Ser Pro Ser Thr Lys Ser
            260                 265                 270

Ser

<210> SEQ ID NO 15
<211> LENGTH: 348
<212> TYPE: DNA
<213> ORGANISM: Chlamydia trachomatis
<220> FEATURE:
<221> NAME/KEY: CDS
<222> LOCATION: (1)..(348)

<400> SEQUENCE: 15 atg gtt cat tct gta tac aat tca ttg gct cca gaa ggt ttt agc caa    48
Met Val His Ser Val Tyr Asn Ser Leu Ala Pro Glu Gly Phe Ser Gln
 1               5                  10                  15 gtc tct att caa ccc agt cag att cca acc agc aaa aaa gta atg att    96
Val Ser Ile Gln Pro Ser Gln Ile Pro Thr Ser Lys Lys Val Met Ile

```
gcg ata atg act ctt ttt gca ctc aca gcc att gca gca ata gtc ctt    144
Ala Ile Met Thr Leu Phe Ala Leu Thr Ala Ile Ala Ala Ile Val Leu
         35                  40                  45 tcc atc gtt aca gtt tgt gga ggg ttt cct ttt ctt ctt gct gca ctt    192
Ser Ile Val Thr Val Cys Gly Gly Phe Pro Phe Leu Leu Ala Ala Leu
 50                  55                  60 aac acc gta act att ggt gca tgc gta tcc ttg ccg gta ttc act tgc    240
Asn Thr Val Thr Ile Gly Ala Cys Val Ser Leu Pro Val Phe Thr Cys
 65                  70                  75                  80 ata gct aca acg tta tta ctt ctt tgt ctc cgt aat atc gaa ctc cta    288
Ile Ala Thr Thr Leu Leu Leu Leu Cys Leu Arg Asn Ile Glu Leu Leu
             85                  90                  95 gcc aga ccg caa gta ttt acc ctc tcc act caa ttc agc cca aca aaa    336
Ala Arg Pro Gln Val Phe Thr Leu Ser Thr Gln Phe Ser Pro Thr Lys
            100                 105                 110 cct caa gaa tag                                                    348
Pro Gln Glu
        115
```

<210> SEQ ID NO 16
<211> LENGTH: 115
<212> TYPE: PRT
<213> ORGANISM: Chlamydia trachomatis

<400> SEQUENCE: 16

```
Met Val His Ser Val Tyr Asn Ser Leu Ala Pro Glu Gly Phe Ser Gln
 1               5                  10                  15

Val Ser Ile Gln Pro Ser Gln Ile Pro Thr Ser Lys Lys Val Met Ile
             20                  25                  30

Ala Ile Met Thr Leu Phe Ala Leu Thr Ala Ile Ala Ala Ile Val Leu
         35                  40                  45

Ser Ile Val Thr Val Cys Gly Gly Phe Pro Phe Leu Leu Ala Ala Leu
 50                  55                  60

Asn Thr Val Thr Ile Gly Ala Cys Val Ser Leu Pro Val Phe Thr Cys
 65                  70                  75                  80

Ile Ala Thr Thr Leu Leu Leu Leu Cys Leu Arg Asn Ile Glu Leu Leu
             85                  90                  95

Ala Arg Pro Gln Val Phe Thr Leu Ser Thr Gln Phe Ser Pro Thr Lys
            100                 105                 110

Pro Gln Glu
        115
```

<210> SEQ ID NO 17
<211> LENGTH: 537
<212> TYPE: DNA
<213> ORGANISM: Chlamydia trachomatis
<220> FEATURE:
<221> NAME/KEY: CDS
<222> LOCATION: (1)..(537)

<400> SEQUENCE: 17

```
atg acg tac tct ata tcc gat ata gca cac aaa tct gat att tct aat    48
Met Thr Tyr Ser Ile Ser Asp Ile Ala His Lys Ser Asp Ile Ser Asn
 1               5                  10                  15 ccc acg tct ccc gct cca tca aga aaa cga gga tcc ttt ccc cca caa    96
Pro Thr Ser Pro Ala Pro Ser Arg Lys Arg Gly Ser Phe Pro Pro Gln
             20                  25                  30 tct cct tct gcc gtg ggc tct tta gag gga gct aat ttc tct aca tgg    144
Ser Pro Ser Ala Val Gly Ser Leu Glu Gly Ala Asn Phe Ser Thr Trp
```

```
                  35                  40                  45
ggg cca ggc ccc ttc ttc act gtc cct gtt tat cca caa caa ctc gct       192
Gly Pro Gly Pro Phe Phe Thr Val Pro Val Tyr Pro Gln Gln Leu Ala
 50                  55                  60 gca atg caa aac aac ctt ttt aca ttg caa aca gag gtt tct gct ctc       240
Ala Met Gln Asn Asn Leu Phe Thr Leu Gln Thr Glu Val Ser Ala Leu
 65                  70                  75                  80 aag aaa aaa tta gtt cag tct agt cag aca cgc gga tct tta gga ctc       288
Lys Lys Lys Leu Val Gln Ser Ser Gln Thr Arg Gly Ser Leu Gly Leu
                 85                  90                  95 ggc ccg cag ttt tta gcg gca tgc tta gtt gct gca aca atc ctt gca       336
Gly Pro Gln Phe Leu Ala Ala Cys Leu Val Ala Ala Thr Ile Leu Ala
                100                 105                 110 gta gct gtt atc gta ctt gct tcc tta gga ctt ggc ggt gtt ctt cct       384
Val Ala Val Ile Val Leu Ala Ser Leu Gly Leu Gly Gly Val Leu Pro
            115                 120                 125 ttt gtc ctt gtt tgt ctg gct ggg tca act aat gca att tgg gct att       432
Phe Val Leu Val Cys Leu Ala Gly Ser Thr Asn Ala Ile Trp Ala Ile
130                 135                 140 gtg agc gcc tcc atc act aca ctg att tgt tgc gtt tcc atc gct tgc       480
Val Ser Ala Ser Ile Thr Thr Leu Ile Cys Cys Val Ser Ile Ala Cys
145                 150                 155                 160 atc ttc tta gca aaa tgt gat aag gga tct gat cct caa act tta tat       528
Ile Phe Leu Ala Lys Cys Asp Lys Gly Ser Asp Pro Gln Thr Leu Tyr
                165                 170                 175 gta agc taa                                                            537
Val Ser <210> SEQ ID NO 18
<211> LENGTH: 178
<212> TYPE: PRT
<213> ORGANISM: Chlamydia trachomatis

<400> SEQUENCE: 18

Met Thr Tyr Ser Ile Ser Asp Ile Ala His Lys Ser Asp Ile Ser Asn
 1               5                  10                  15

Pro Thr Ser Pro Ala Pro Ser Arg Lys Arg Gly Ser Phe Pro Pro Gln
                20                  25                  30

Ser Pro Ser Ala Val Gly Ser Leu Glu Gly Ala Asn Phe Ser Thr Trp
            35                  40                  45

Gly Pro Gly Pro Phe Phe Thr Val Pro Val Tyr Pro Gln Gln Leu Ala
 50                  55                  60

Ala Met Gln Asn Asn Leu Phe Thr Leu Gln Thr Glu Val Ser Ala Leu
 65                  70                  75                  80

Lys Lys Lys Leu Val Gln Ser Ser Gln Thr Arg Gly Ser Leu Gly Leu
                 85                  90                  95

Gly Pro Gln Phe Leu Ala Ala Cys Leu Val Ala Ala Thr Ile Leu Ala
                100                 105                 110

Val Ala Val Ile Val Leu Ala Ser Leu Gly Leu Gly Gly Val Leu Pro
            115                 120                 125

Phe Val Leu Val Cys Leu Ala Gly Ser Thr Asn Ala Ile Trp Ala Ile
130                 135                 140

Val Ser Ala Ser Ile Thr Thr Leu Ile Cys Cys Val Ser Ile Ala Cys
145                 150                 155                 160

Ile Phe Leu Ala Lys Cys Asp Lys Gly Ser Asp Pro Gln Thr Leu Tyr
                165                 170                 175

Val Ser
```

```
<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 19
agaaccgatt taactccagg cg                                              22

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 20
gcgcggatcc ttaatgtccg gtaggcctag                                      30

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 21
atgtcaacaa caccagcatc ttc                                             23

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: PCR primer

<400> SEQUENCE: 22
gcgcggatcc ttaattagtg ccttctggat tagg                                 34

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 23
cgcagtactg tatccacaga caac                                            24

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 24
gtcggatccg agaaactctc catgcc                                          26
```

CHLAMYDIA PROTEINS AND THEIR USES

CROSS REFERENCE TO RELATED APPLICATIONS

This is a National Stage of International Application No. PCT/US99/08744, filed Apr. 20, 1999, which claims the benefit of U.S. Provisional Applications No. 60/082,438, filed Apr. 20, 1998, Ser. No. 60/082,588, filed Apr. 21, 1998, and Ser. No. 60/086,450, filed May 22, 1998.

I. FIELD OF THE INVENTION

The present invention relates to the detection of Chlamydia and to the diagnosis, treatment and prevention of Chlamydia infections in animals.

II. BACKGROUND

Chlamydiae are obligate intracellular bacterial pathogens with a unique biphasic life cycle. They appear as two distinct cellular types, a small dense cell or elementary body (EB) that is enclosed in a rigid bacterial cell wall, and a larger metabolically active reticulate body (RB). The EB is resistant to physical disruption and is infectious, whereas the RB is more fragile and only exists inside cells. The Chlamydia life cycle begins with the attachment of the EB form to the host cell which is followed by endocytosis into a nascent vacuole, also called an "inclusion membrane". After EB attachment and entry, replication of the EB form produces RB forms that continue to grow within the vacuole. By 72 hour post-infection, this growth phase is terminated when the RBs condense, and reorganize back to EBs. The lysis of the host cell results in release of EBs to infect new host cells. The difficulties in working with Chlamydiae center on the obligate intracellular requirement for growth and the fact that no adequate genetic engineering methods have been developed for this organism.

The genus Chlamydia includes two species that are primarily associated with human disease: *C. trachomatis* and *C. pneumoniae*. *C. trachomatis* causes trachoma, an eye disease that is the leading cause of preventable infectious blindness worldwide with an estimated 500 million cases of active trachoma worldwide. *C. trachomatis* also causes a sexually transmitted chlamydial disease which is very common worldwide. *C. trachomatis* also causes lymphogranuloma venereum, a debilitating systemic disease characterized by lymphatic gland swelling. The most serious sequelae of chlamydial genital infections of females include salpingitis, pelvic inflammatory disease, and ectopic pregnancy. In the U.S. alone, it is estimated that over 4 million new sexually transmitted *C. trachomatis* infections occurred in 1990, leading to over four billion dollars in direct and indirect medical expenses. The World Health Organization estimates that 89 million new cases of genital Chlamydia occurred worldwide in 1995 (Peeling and Brunham, 1996).

*C. pneumoniae* causes respiratory diseases including so called walking pneumonia, a low-grade disease such that the infected person frequently fails to obtain treatment and remains in the community as an active, infectious carrier. *C. pneumoniae* is currently of interest because of its strong epidemiological association with coronary artery disease, and there is also some evidence to link it with multiple sclerosis.

Of the other disease-causing species of Chlamydia, *Chlamydia psittaci* and *Chlamydia pecorum* are primarily pathogens of wild and domestic animals, but these species may infect humans accidentally. *C. psittaci* is acquired through respiratory droplet infection and is considered an occupational health hazard for bird fanciers and poultry workers.

There is tremendous interest in the identification of candidate antigens for protection against chlamydial disease. While a prior infection with *C. trachomatis* will protect against a subsequent challenge by the same strain, indicating a protective component that stimulates the host immune response, most serious chlamydial diseases are exacerbated by an overaggressive anti-chlamydial immune response. Antigens recognized in the context of an infection appear to elicit a protective response whereas immunization with purified, killed (EB form) Chlamydia results in an immunopathological response. Therefore for the purposes of vaccine development, one needs to find epitopes that confer protection, but do not contribute to pathology. It is an object of this invention to provide Chlamydia polypeptides for use as vaccines that induce a protective immune response without inducing the pathological response caused by the antigens associated with the EB form of Chlamydia. Such immunostimulatory peptides will be useful in the treatment, as well as in the diagnosis, detection and prevention of Chlamydial infections.

III. SUMMARY OF THE INVENTION

The present invention includes the use of Chlamydia proteins that show enhanced expression in the reticulate body (RB) stage relative to the elementary body (EB) stage of the Chlamydia life cycle. These proteins are not present at detectable levels in the EB form using current immunological techniques and are thus said to be "infection-specific." Certain of these infection-specific proteins are found in the inclusion membrane of the infected cell, and so have been termed "Inc" proteins. These include the IncA, IncB, and IncC proteins of Chlamydia as described in the present disclosure. The genes that encode the IncA, IncB and IncC proteins are referred to as incA, incB and incC respectively. Other proteins of Chlamydia described herein have also been shown by the inventors to be infection-specific, but are not known to be incorporated into the inclusion membrane; these include the p242, TroA, and TroB proteins. The TroA and TroB proteins have been so named because they resemble the Tro proteins of *Treponema pallidum*, which are thought to form part of an ABC transport system.

The inventors have shown that the infection-specific Chlamydia proteins of the disclosure are recognized by convalescent antisera (i.e., antisera taken from an animal that has recovered from a Chlamydia infection) but are not recognized by antisera against the killed EB form of Chlamydia. Thus, the proteins are expressed only during active chlamydial infection and are therefore useful as protective antigens. These infection-specific proteins may be used to confer a protective immune response without inducing a pathological effect. Additionally, immuno-fluorescence microscopy and immunoblotting with antisera demonstrated that the infection-specific proteins are present in Chlamydia-infected HeLa cells, but are undetectable in purified EBs and absent in uninfected HeLa cells.

Immunofluorescense microscopy reveals that IncA, IncB and IncC are localized to the inclusion membrane of infected HeLa cells. Reverse-transcription polymerase chain reactions (RT-PCR), northern hybridization data, and restriction analysis revealed that the incB and incC genes are closely linked and transcribed in an operon. RT-PCR, restriction analysis and sequential Southern hybridizations of incA then incC to the same filter provided evidence that incA is separated from the incB and incC operon by about 110 kb. The *C. trachomatis* Tro genes are not closely linked with the p242 gene.

The present invention includes the nucleotide and amino acid sequences for certain infection-specific proteins from Chlamydia. These proteins are p242, TroA, and TroB from *C. trachomatis*, and the IncB, and IncC proteins from *C. psittaci*. The scope of the invention includes fragments of these proteins that may be used in a vaccine preparation or that may be used in a method of detecting Chlamydia antibodies. Such fragments may be, for example, 5, 10, 15, 20, 25, or 30 contiguous amino acids in length. They may even encompass the entire protein.

More specifically, the present invention encompasses the purified infection-specific proteins having amino acid sequences as shown in SEQ ID NOS: 2, 4, 6, 10, and 12, amino acid sequences that differ from such sequences by one or more conservative amino acid substitutions, and amino acid sequences that show at least 75% sequence identity with such amino acid sequences.

Then invention also includes isolated nucleic acid molecules that encode a protein as described in the above paragraph, including isolated nucleic acid molecules with nucleotide sequences as shown in SEQ ID NOS: 1,3, 5, 9, and 11.

The present invention also includes a vaccine or immunostimulatory preparation directed against the reticulate body (RB) form of Chlamydia comprising one or more purified infection-specific peptides (or portions or fragments thereof, or peptides showing sequence similarity to a portion of such a peptide). Such peptide fragments may be, for example, 5, 10, 15, 20, 25, or 30 contiguous amino acids in length, of the sequence shown in SEQ ID NOS: 2, 4, 6, 8, 10, 12, 14, 16, or 18. Peptides used in such a vaccine may even encompass the entire purified:!peptide of SEQ ID NOS: 2, 4, 6, 8, 10, 12, 14, 16, or 18, a peptide that differs from such a peptide by one or more conservative amino acid substitutions, or a peptide having at least 75% sequence identity with such a peptide. Such vaccine preparations may contain one or more pharmaceutically acceptable excipients, adjuvants or diluents.

The invention additionally encompasses methods for making a vaccine, comprising combining a pharmaceutically acceptable excipient with a peptide described herein. Also included is a method of vaccination comprising administering a vaccine as described herein to a mammal.

The present invention also provides a method for the diagnostic use of the disclosed purified infection-specific peptides, for instance by use in a diagnostic assay to detect the presence of infection-specific antibodies in a medical specimen, in which antibodies bind to the Chlamydia peptide and indicate that the subject from which the specimen was removed was previously exposed to Chlamydia. Such a method may comprise: (i) supplying a biological sample, such as blood from an animal, that is suspected to contain infection-specific anti-Chlamydia antibody, (ii) contacting the sample with at least one infection-specific Chlamydia peptide described herein, such that a reaction between the peptide and the infection-specific anti-Chlamydia antibody gives rise to a detectable effect, such as a chromogenic conversion; and (iii) detecting this detectable effect.

The present invention also provides a method of using antibodies that bind specifically with the disclosed proteins for detection of infection-specific Chlamydia antigen, indicating the presence of Chlamydia in the RB stage as distinct from the EB stage. For instance, the relevant infection-specific antibodies may be used to provide specific binding in an Enzyme Linked Immunosorbant Assay (ELISA) or other immunological assay wherein the antibody $F_c$ portion is linked to a chromogenic, fluorescent or radioactive molecule and the $F_{ab}$ portion specifically interacts with, and binds to, an infection-specific protein. Such a method may comprise: (i) supplying a biological sample from an animal suspected to contain an infection-specific Chlamydia antigen, and (ii) contacting the sample with at least one infection-specific anti-Chlamydia antibody, such that a reaction between the antibody and the infection-specific Chlamydia protein gives rise to a detectable effect; and (iii) detecting this detectable effect.

Other aspects of the present invention include the use of probes and primers derived from the nucleotide sequences that encode infection-specific peptides, to detect the presence of Chlamydia nucleic acids in medical specimens. Such probes and primers may be nucleotide fragments, of, for example, 15, 20, 25, 30 or 40 contiguous nucleotides of the sequence shown in SEQ ID NOS: 1, 3, 5, 7, 9, 11, 13, 15, or 17.

An additional aspect of the invention is a method of treating a Chlamydia infection by directing a therapeutic agent against a specific target, where the target is chosen from an infection specific protein of Chlamydia, a gene that encodes an infection-specific protein of Chlamydia, and an RNA transcript that encodes an infection-specific protein of Chlamydia, wherein the therapeutic agent interacts with said target to affect a reduction in pathology.

These and other aspects of the invention will become more apparent from the following description.

IV. SEQUENCE LISTING

SEQ ID NO:1 shows a nucleic acid sequence encoding the p242 *C. trachomatis* protein, with deduced primary amino acid sequence also shown.

SEQ ID NO:2 shows the amino acid sequence of the p242 *C. trachomatis* protein.

SEQ ID NO:3 shows a nucleic acid sequence encoding the TroA *C. trachomatis* protein, with deduced primary amino acid sequence also shown.

SEQ ID NO:4 shows the amino acid sequence of the TroA *C. trachomatis* protein.

SEQ ID NO:5 shows a nucleic acid sequence encoding the TroB *C. trachomatis* protein, with deduced primary amino acid sequence also shown.

SEQ ID NO:6 shows the amino acid sequence of the TroB *C. trachomatis* protein.

SEQ ID NO:7 shows a nucleic acid sequence encoding the IncA *C. psittaci* protein, with deduced primary amino acid sequence also shown.

SEQ ID NO:8 shows the amino acid sequence of the IncA *C. psittaci* protein.

SEQ ID NO:9 shows a nucleic acid sequence encoding the IncB *C. psittaci* protein, with deduced primary amino acid sequence also shown.

SEQ ID NO:10 shows the amino acid sequence of the IncB *C. psittaci* protein.

SEQ ID NO:11 shows a nucleic acid sequence encoding the IncC *C. psittaci* protein, with deduced primary amino acid sequence also shown.

SEQ ID NO:12 shows the amino acid sequence of the IncC *C. psittaci* protein.

SEQ ID NO:13 shows a nucleic acid sequence encoding the IncA *C. trachomatis* protein, with deduced primary amino acid sequence also shown.

SEQ ID NO:14 shows the amino acid sequence of the IncA *C. trachomatis* protein.

SEQ ID NO:15 shows a nucleic acid sequence encoding the IncB *C. trachomatis* protein, with deduced primary amino acid sequence also shown.

SEQ ID NO:16 shows the amino acid sequence of the IncB *C. trachomatis* protein.

SEQ ID NO:17 shows a nucleic acid sequence encoding the IncC *C. trachomatis* protein, with deduced primary amino acid sequence also shown.

SEQ ID NO: 18 shows the amino acid sequence of the IncC *C. trachomatis* protein.

SEQ ID NO: 19 shows the upstream oligonucleotide used to amplify the *C. psittaci* incC ORF.

SEQ ID NO:20 shows the downstream oligonucleotide used to amplify the *C. psittaci* incC ORF.

SEQ ID NO:21 shows the upstream oligonucleotide used to amplify the *C. psittaci* incB ORF.

SEQ ID NO:22 shows the downstream oligonucleotide used to amplify the *C. psittaci* incB ORF.

SEQ ID NO:23 shows the upstream oligonucleotide used to amplify the *C. psittaci* incA ORF.

SEQ ID NO:24 shows the downstream oligonucleotide used to amplify the *C. psittaci* incA ORF.

V. DESCRIPTION OF THE INVENTION

A. Definitions

Particular terms and phrases used herein have the meanings set forth below.

"EB" refers to the Elementary Body, an environmentally refractile and largely metabolically dormant form of Chlamydia that is infectious and is presented as a small dense body enclosed by a bacterial cell wall.

"RB" refers to the Reticulate Body, a metabolically active form of Chlamydia that is not infectious, and exists only within a host cell being very fragile, often branched, and appearing larger and less dense that the EB.

"Infection-specific" refers to a protein that shows enhanced expression in the RB form of Chlamydia compared to the EB form. Infection-specific proteins are not necessarily absent from the EB form, but they are significantly more common in the RB form than in the EB form.

"infection-specific antibody" is an antibody that binds specifically to an infection-specific protein.

"Biological sample" refers to any sample of biological origin including, but not limited to a blood sample, a plasma sample, a mucosal smear or a tissue sample.

"Isolated" An isolated nucleic acid has been substantially separated or purified away from other nucleic acid sequences in the cell of the organism in which the nucleic acid naturally occurs, i.e., other chromosomal and extrachromosomal DNA and RNA. The term "isolated" thus encompasses nucleic acids purified by standard nucleic acid purification methods. The term also embraces nucleic acids prepared by recombinant expression in a host cell as well as chemically synthesized nucleic acids.

"Probes" and "primers." Nucleic acid probes and primers may readily be prepared based on the nucleic acid sequences provided by this invention. A "probe" comprises an isolated nucleic acid attached to a detectable label or reporter molecule. Typical labels include radioactive isotopes, ligands, chemiluminescent agents, and enzymes.

"Primers" are short nucleic acids, typically DNA oligonucleotides 15 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

Probes and primers as used in the present invention typically comprise at least 15 nucleotides of the nucleic acid sequences that are shown to encode infection-specific proteins. In order to enhance specificity, longer probes and primers may also be employed, such as probes and primers that comprise at least 20, 30 or 40 consecutive nucleotides of the disclosed nucleic acid sequences.

Methods for preparing and using probes and primers are well known in the art and are described in, for example Sambrook et al. (1989); Ausubel et al., (1987); and Innis et al., (1990). PCR primer pairs can be derived from a known sequence, for example, by using computer programs intended for that purpose such as Primer (Version 0.5, 1991, Whitehead Institute for Biomedical Research, Cambridge, Mass.).

"Conservative amino acid substitutions" are those substitutions that, least interfere with the properties of the original protein, i.e., the structure and especially the function of the protein is conserved and not significantly changed by such substitutions. The table below shows amino acids which may be substituted for an original amino acid in a protein and which are regarded as conservative substitutions.

| Original Residue | Conservative Substitution |
|---|---|
| Ala | Ser |
| Arg | Lys |
| Asn | gln, his |
| Asp | Glu |
| Cys | Ser |
| Gln | Asn |
| Glu | Asp |
| Gly | Pro |
| His | asn, gln |
| Ile | leu, val |
| Leu | ile, val |
| Lys | arg, gln, glu |
| Met | leu, ile |
| Phe | met, leu, tyr |
| Ser | Thr |
| Thr | Ser |
| Trp | Tyr |
| Tyr | trp, phe |
| Val | ile, leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, e.g., seryl or threonyl, is substituted for (or by) a hydrophobic residue, e.g., leucyl, isoleucyl, phenylalnyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

"Sequence identity" The similarity between two nucleic acid sequences, or two amino acid sequences is expressed in terms of the level of sequence identity shared between the sequences. Sequence identity is typically expressed in terms of percentage identity; the higher the percentage, the more similar the two sequences are. Variants of naturally occurring infection-specific peptides useful in the present invention are typically characterized by possession of at least 50% sequence identity counted over the full length alignment with the amino acid sequence of a naturally occurring infection-specific peptide when aligned using BLAST 2.0.1 (Altschul et al., 1997). For comparisons of amino acid sequences of greater than about 30 amino acids, the BLAST 2 analysis is employed using the blastp program set to default perameters (open gap=11, extension gap=1 penalty, gap×dropoff=50, expect=10, word size=3, filter on), and using the default BLOSUM62 matrix (gap existence cost= 11, per residue gap cost=1 lambda ratio =0.85). When aligning short peptides (fewer than around 30 amino acids), the alignment should be performed using the Blast 2 sequences function, employing the PAM30 matrix (gap existence cost=9, per residue gap cost=1, lambda ratio= 0.87). Proteins with even greater similarity to the reference sequences will show increasing percentage identities when assessed by this method, such as at least 60%, at least 70%, at least 80%, at least 85%, at least 90%, or at least 95% sequence identity. The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at http//www.ncbi.nlm.nih.gov/BLAST/. A description of how to determine sequence identity using this program is available at http://www.ncbi.nlm.nih.gov/BLAST/blast help.html.

Similarly, when comparing nucleotides, blastn may be used with default settings (rewards for match=1, penalty for mismatch=−2, open gap=5. extension gap=2 penalty, gap× dropoff=50, expect=10, word size=11, filter on), with the default BLOSUM62 matrix (as above). Variants of naturally occurring infection-specific nucleic acid sequences useful in the present invention are typically characterized by possession of at least 50% sequence identity counted over the full length alignment with the nucleic acid sequence of a naturally occurring infection-specific ORF when aligned using BLAST 2.0.1. Useful nucleic acids may show even greater percentage identity, and may, for example, possess at least 55%, at least 65%, at least 75%, at least 80%, at least 85%, at least 90%, or at least 95% sequence identity naturally occurring infection-specific ORF.

"Operably linked" A first nucleic acid sequence is "operably" linked with a second nucleic acid sequence when the first nucleic acid sequence is placed in a functional relationship with the nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Recombinant" A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

"Stringent Conditions" Stringent conditions, in the context of nucleic acid hybridization, are sequence-dependent and are different under different environmental parameters. Generally, stringent conditions are selected to be about 5 degrees to 20 degrees lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al. (1989), pages 9.49–9.55. Typical high stringency hybridization conditions (using radiolabeled probes to hybridize to nucleic acids immobilized on a nitrocellulose filter) may include, for example, wash conditions of 0×SSC, 0.5% SDS at a wash temperature of 68° C.

When referring to a probe or primer, the term "specific for (a target sequence)" indicates that the probe or primer hybridizes under high-stringency conditions substantially only to the target sequence in a given sample comprising the target sequence.

"Purified" A purified peptide is a peptide that has been extracted from the cellular environment and separated from substantially all other cellular peptides. As used herein, the term peptide includes peptides, polypeptides and proteins. In certain embodiments, a purified peptide is a preparation in which the subject peptide comprises 50% or more of the protein content of the preparation. For certain uses, such as vaccine preparations, even greater purity may be preferable.

"Immunostimulatory peptide" as used herein refers to a peptide that is capable of stimulating a humoral or antibody-mediated immune response when inoculated into an animal.

"Vaccine" A vaccine is a composition containing at least one immunostimulatory peptide which may be inoculated into an animal with the intention of producing a protective immunological reaction against a certain antigen. The antigen to be protected against may be, for instance, an infection-specific antigen of Chlamydia.

B. Isolation of Infection Specific Chlamydia Polpeptides and Identification of Genes Encoding these Polypeptides Isolation of IncA, IncB and IncC Bacterial strains. Chlamydia (*C. psittaci* strain GPIC or *C. trachomatis* LGV-434, ser. L2) was cultivated in HeLa 229 cells using standard methods (Caldwell et al., 1981). Purified Chlamydia were obtained using Renografin (E. R. Squibb & Sons, Inc., Princeton, N.J.) density gradient centrifugation. *Escherichia coli* DH5α (Bethesda Research Laboratories, Inc., Gaithersburg, Md.) was used as the host strain for transformations with recombinant DNA. *E. coli* XL1-Blue MRF' (Stratagene, La Jolla, Calif.) was used as the host strain for infection with lambda ZAPII phage vector. *E. coli* SOLR (Stratagene) was used as the host strain for infection with in vivo excised filamentous lambda ZAPII.

Antisera. MBP (Maltose Binding Protein)-Inc fusion proteins were used as antigens for the production of monospecific antibody reagents in Hartley strain guinea-pigs. The protein was diluted to 100 $\mu g/ml^{-1}$ sterile saline and mixed with the Ribi Trivalent Adjuvant (Ribi Immunochem.). The antigen/adjuvant emulsion was administered to anaesthetized guinea-pigs using a procedure provided by the manufacturer. Sera were collected 14 days after secondary and tertiary immunizations. Control antisera were produced by immunizing guinea-pigs with adjuvant alone, or with adjuvant plus purified maltose-binding protein.

Convalescent guinea-pig antisera, antisera against live EBs, and antisera against formalin-fixed EBs were produced using standard methods (Rockey and Rosquist, 1994 and. Rockey et al., 1995).

*C. psittaci* library construction and screening. For the incB and incC genes, *C. psittaci* strain GPIC DNA was extracted using a genomic DNA extraction kit (Qiagen) with one modification; dithiothreitol (5 mM) was added to the suspension buffer to assist EB lysis. DNA was partially digested with Tsp509I and ligated to EcoRI digested λ-ZAPII phage arms (Stratagene). The ligation was packaged in vitro with Gigapack extracts accordinglito the manufacturer's instructions (Stratagene). Recombinant phage were plated on *E. coli* XL-1 Blue at densities of approximately $10^4$ PFU/150mm (diameter) plate. Following a nine hour incubation to allow development of the plaques, the plates were sequentially overlaid with nitrocellulose disks and the resulting lifts were processed for immunoblotting with convalescent antisera and antisera to fixed EBs. Of approximately 8,000 plaques, 18 had reactivity with the convalescent sera but not sera generated against EBs. One of these was subcloned into pBluescript SK(−) phagmid by in vitro excision in the *E. coli* SOLR strain (Stratagene) and designated pBS200-7.

For the incA gene, genomic DNA from *C. psittaci* strain GPIC was partially digested with Sau3A, size-selected (2–8 kb) by electrophoresis through low-melting-temperature agarose, and blunt-ended with T4 DNA polymerase. This DNA was ligated to an EcoR1/Not1 adapter (Life Technologies), kinased, and ligated to EcoR1-digested Lambda ZAP II vector (Stratagene Cloning Systems). Recombinants were packaged (Lambda Gigapack Gold, Stratagene) and used to infect *E. coli* XL1-Blue (Stratagene). Plaques were allowed to develop for 4 h at 37° C. Nitrocellulose filters laden with 10 mM IPTG (U.S. Biochemical Corp.) were placed onto the plaques and incubated for an additional 4 h at 37° C. These filters were removed and placed into a blocking solution consisting of PBS (150 mM NaCl, 10 mM $NaPO_4$, pH7.2) plus 0.1% Tween-20 (TPBS) and 2% BSA-TPBS. Filters were incubated for 1 h, rinsed twice in TPBS, and incubated overnight in convalescent-guinea-pig sera diluted 1:100 in BSA-TPBS. After three washes in TPBS, the filters were incubated for 1 h in $^{125}$I-staphylococcal protein A (New England Nuclear) diluted to approx. 124 nCiml$^{-1}$ in BSA-TPBS. Filters were again washed three times in TPBS and positive plaques were detected by exposure of the dried filters to autoradiography film overnight at room temperature. Positive clones were picked and plaque-purified. pBluescript-SK-plasmids containing the chlamydial genes of interest were recovered from the purified bacteriophage using ExAssist filamentous bacteriophages (Stratagene).

Identification of antigens recognized by convalescent antisera. Recombinant plaques were identified that showed reactivity with convalescent (anti-RB) antisera, but not with anti-EB serum. The purified recombinant phage were converted into pBluescriptII SK plasmid by in vivo excision and recircularization and these recombinant DNAs were used to transform *E. coli*. SDS-PAGE and immunoblot analysis of lysates of these recombinant *E. coli* showed that each expressed one or more proteins that reacted with convalescent antisera but not with the EB serum.

DNA Cloning and fusion protein production. The plasmid pJC2 contain's a 5.0 kb EcoRI GPIC genomic fragment cloned into the pZEro2.1 vector (Invitrogen). To construct pJC2, the incC ORF sequence was $^{32}$P-radiolabeled using random priming (Gibco-BRL) and used to probe EcoRI cut GPIC genomic DNA fragments separated by agarose gel electrophoresis. Fragments in the size range of the positive signal were excised from the gel and purified by Gene-Clean (Bio101). The gel-purified fragments were used in a ligation along with EcoRI-digested pZEro2.1. Kanamycin resistant colonies were screened by colony hybridization with radiolabeled incC.

MBP fusions of the five ORFs present in pJC2 were produced using the pMAL-C2 vector (New England Biolabs). The reading frame of incC, with the exception of the first four codons, was amplified using Pwo polymerase (Boehringer Mannheim) and pBS200-7 as the template. The upstream and downstream oligonucleotides for this amplification were 5'-AGAACCGATTTAACTCCAGGCG-3' (SEQ ID NO: 19) and 5'-GCGCGGATCCTTAATGTCCGGTAGGCCTAG-3' (SEQ ID NO: 20), respectively.

The vector was digested with XmnI and BamHI, and the amplication product was digested with BamHI. Ligation of these products resulted in an in-frame fusion between the malE gene in the vector and the incC reading frame from pBS200-7. The stop codon for this construction is provided by the insert. Following ligation, the products were transformed into *E. coli* strain HD5α. The resulting fusion protein (MBP/IncC) was overexpressed and purified by maltose affinity chromatography using an amylose resin supplied by New England Biolabs.

The same approach was used for production of the MBP/IncB fusion protein. The sequence encoding the N-terminal 101 amino acids of the IncB ORF was PCR amplified using the oligonucleotides 5'-ATGTCAACAACACCAGCATCTTC-3' (SEQ ID NO: 21) and

5'-GCGCGGATCCTTAATTAGTGCCTTCTGGATTAG G-3' (SEQ ID NO: 22).

The purified MBP/IncB and MBP/IncC fusion proteins were used as antigen for the production of monospecific antibody in Hartley strain guinea-pigs by standard methods (Rockey et al., 1995). Inserts in each construct were confirmed by DNA sequencing.

For IncA, a maltose-binding protein/IncA fusion protein was produced using the pMAL-C2 vector system from New England Biolabs. The reading frame of incA shown in FIG. 1, with the exception of the initiator ATG, the incA ORF was amplified using Vent DNA polymemase (New England Biolabs) and plasmid pGP17 as template. The upstream and downstream ogligo-nucleotides for this amplification were 5'-CGCAGTACTGTATCCACAGACAAC-3' (SEQ ID NO: 23) and 5'-GTCGGATCCGAGAAACTCTCCATGCC-3' (SEQ ID NO: 24), respectively. The vector was digested with XmnI and BamHI, and the amplification product was digested with ScaI and BamHI. Ligation of these products resulted in an in-frame fusion between the malE gene in the vector and the incA reading frame from pGP17. The stop codon for this construction is provide by the insert. Following ligation, the products were transformed into *E. coli* strain DH5α. The resulting fusion protein (MBP/IncA) was overexpressed and purified by maltose affinity chromatography using amylose resin (New England Biolabs).

MBP/IncA was used as antigen for the production of monospecific antibody reagents in Hartley strain guinea-pigs.

DNA sequencing and sequence analysis. The pBS200-7 and pJC2 genomic clones as well as the MBP fusions were sequenced with the Taq DyeDeoxy Terminator Cycle Sequencing Kit (Perkin Elmer/Applied Biosystems Division). Several internal primers were designed to sequence further into the cloned inserts. Sequence assembly was performed using AssemblyLIGN software and sequence analysis was performed with MacVector software (International. Biotechnologies Incorporated). Hydrophilicity profiles were determined using the Kyte-Doolittle scale (Kyte and Doolittle, 1982) with a window of 7. Deduced amino acid sequences were compared with the database using the BLAST program (on default settings) available from the National Center for Biotechnology Information on the world wide web. The entire nucleotide sequence of the pJC2 insert was deposited in the GenBank/EMBL Nucleotide Sequence Data Library, under accession number AF017105.

For incA, nucleotide sequencing was conducted using the Sequences system, (US Biochemical) with the M13 forward and reverse primers, and internal primers synthesized on an Milligen/Biosearch Cyclone Plus DNA synthesizer. Computer analyses were conducted using the MacVector Sequence Analysis Software (International Biotechnologies Incorporated). Hydrophilicity profiles were determined using the Kyte-Doolittle scale (Kyte and Doolittle, 1982) with a window of 7. Secondary-structure predictions were generated using a combination of the Chou-Fasman and Robson-Garnier methods (Robson and Suzuki, 1976; Chou and Fasman, 1978). Deduced amino acid sequences were compared with those in the EMBL and GenBank databases using the BLASTP program available from the National Center for Biotechnology Information.

Electrophoresis and immunoblotting. Polyacrylamide gel electrophoresis (PAGE) was conducted using standard methods (Rockey and Rosquist, 1994). Immunoblotting was performed using standard methods (Rockey et al., 1995).

Immunofluorescence studies. Chlamydiae grown in HeLa cells on sterile glass coverslips were fixed for microscopy one of two ways. Cells were either incubated in methanol for 5 minutes, or in the combination fixative periodate-lysine-paraformaldephyde (PLP) for three hours at room temperature followed by permeabilization with 0.05% saponin (Brown and Farquhar, 1989). Immunostaining of the fixed coverslips was performed according to standard methods (Rockey et al., 1995) and visualized under a Nikon Microphot FXA microscope using the 63× objective and oil immersion.

RT-PCR analysis. RNA for RT-PCR analysis was extracted from approximately $2 \times 10^{14}$ C. psittaci-infected cells. A Qiagen column was used for extraction and purification according to the manufacturer's instructions (Qiagen). RQ1 RNase DNase (Promega) was used to ensure removal of contaminating genomic DNA. cDNA was prepared by incubating 1.5 μg of RNA, 2.5 μM of the reverse oligonucleotide primer, and AMV reverse transcriptase (Promega) for 1 hour at 42° C. in sodium pyrophosphate buffer, according to the manufacturer's instructions. PCR reactions were carried out using 1 $\mu$l of the cDNA reaction, 1.25 $\mu$M of each oligonucleotide primer, and Pwo polymerase (Boehringer Mannheim). Each RT-PCR reaction was accompanied by a positive control reaction that utilized the same primer set and 10 ng of *C. psittaci* genomic DNA, and a negative control reaction in which 1 $\mu$l of the same RNA preparation was used as template in the PCR reaction. A control primer set located within the incC gene was also used as an RT-PCR control.

Identification of incA, incB and incC genes of *C. trachomatis*. The nucleotide sequence information obtained for the incA, incB and incC of *C. psittaci* (above) was used, with standard methods, to identify the inc gene orthologues of *C. trachomatis*. Probes were made that corresponded to the 3' and 5' ends of the *C. psittaci* inc open reading frames. Standard PCR amplification (as above) was used, with the *C. trachomatis* genome as a template, to amplify the corresponding *C. trachomatis* nucleotide sequence. The amplified DNA was then sequenced, using standard methods.

2. Isolation of p242, TroA and TroB

Bacterial strains. *C. trachomatis* LGV-434, serotype L12, was cultivated in HeLa 229 cells using standard methods (Caldwell et al., 1981). Purified chlamydiae were obtained using Renografin (E. R. Squibb & Sons Inc., Princton, N.J.) density gradient centrifugation (Hackstadt et al., 1992). *Escherichia coli* DH5α (Bethesda Research Laboratories, Inc., Gaithersburg, Md.) was used as the host strain for transformations with recombinant DNA. *E. coli* XL1-Blue MRF' (Stratagene, La Jolla, Calif.) was used as the host strain for infection with lambda ZAPII phage vector. *E. coli* SOLR (Stratagene) was used as the host strain for infection with in vivo excised filamentous lambda ZAPII.

Antisera. Two Cynomolgus monkeys (*Macaca fasicularis*) were anaesthetized and infected urethrally with *C. trachomatis* EBs. Each monkey was infected twice and allowed to recover between infections. Symptoms of infection were monitored over time. Antisera from infected monkeys were tested for reactivity to Chlamydia by ELISA (Su et al., 1990).

Sera were collected every two weeks and anti-chlamydial titers were determined. These animals showed mild clinical signs of disease which cleared spontaneously. A second challenge was then administered. Sera were collected from these animals and used to probe a *C. trachomatis* expression library as discussed below. As a control, Guinea Pigs were immunized with killed *C. trachomatis* of the EB form. Sera from these animals were obtained and also used to probe the *C. trachomatis* expression library.

*C. trachomatis* library construction and immunoscreening. A *C. trachomatis* genomic library was constructed with the lambda ZAPII vector as described above for *C. psittaci*. Approximately 15,000 plaques were plated, transferred to nitrocellulose filters (Schleicher and Schuell, Keene, N. H.) in duplicate, and probed with the monkey convalescent antiserum and with Guinea Pig serum against killed EBs (Bannantine et al., 1998). Plaques that reacted only with the monkey convalescent antisera were selected for further study.

Identification of antigens recognized by convalescent antisera. Four positive recombinant plaques were identified that showed reactivity with convalescent antisera but not with anti-EB serum. The purified recombinant phage were converted into pBluescriptII SK plasmid by in vivo excision and recircularization and these recombinant DNAs (pCt1, pCt2, pCt3 and pCt4) were used to transform *E. coli*. SDS-PAGE and immunoblot analysis of lysates of these recombinant *E. coli* showed that each expressed one or more proteins that reacted with convalescent (anti-RB) antisera but not with the anti-EB antiserum. Two of the recombinants clones, pCt2 and pCt3, expressed an identical 19.9 kDa protein (p242). The pCt4 recombinant expressed two different proteins of approximately 32 kDa each that are strongly recognized by convalescent antisera (TroA and TroB).

C. Sequence Analysis

Sequence analysis of pCt1, 2, and 3 revealed overlapping inserts with only one open reading frame (ORF) common in all three. This ORF encodes an approximately 19.9 kDa protein (p242) that shows no similarity to other known proteins. The nucleotide sequence encoding C. trachomatis p242, and the amino acid sequence of the protein are shown in SEQ ID NOS: 1 and 2, respectively.

The insert in pCt4 contains two complete ORFs which code for two proteins, each of approximately 32 kDa (TroA and TroB) that show some homology with proteins from *Treponema pallidum*. The nucleotide sequences encoding the 32 kDa proteins (TroA and TroB) and the amino acid sequences of these proteins are shown in SEQ ID NOS: 3, 4, 5, and 6.

D. Embodiments of the Invention

The present invention includes the nucleotide and amino acid sequences for certain infection-specific proteins from Chlamydia. These proteins are p242, TroA, and TroB from *C. trachomatis*, and the IncB, and IncC proteins from *C. psittaci*. The scope of the invention includes fragments of these proteins that may be used in a vaccine preparation or that may be used in a method of detecting Chlamydia antibodies. Such fragments may be, for example, 5, 10, 15, 20, 25, or 30 contiguous amino acids in length, or may even encompass the entire protein.

The present invention also encompasses the use of infection-specific proteins of Chlamydia, and the use of nucleotides encoding such proteins. Infection-specific proteins include the IncA, IncB and IncC proteins of *C. psittaci*, the IncA, IncB and IncC proteins of *C. trachomatis*, and the TroA, TroB, and p242 proteins of *C. trachomatis*. The inventors have shown that these proteins are infection-specific by using immunological techniques such as immuno-fluorescence microscopy and immunoblotting.

The present invention includes a vaccine against chlamydial infections comprising infection-specific proteins or fragments of these proteins or proteins that are homologous or show substantial sequence similarity to these proteins. In one embodiment, one or more purified infection-specific proteins may be mixed with a pharmaceutically acceptable excipient to produce a vaccine that stimulates a protective immunological response in an animal. In one embodiment the vaccine may be administered intra-muscularly or subcutaneously or intravenously. In another embodiment, the vaccine may be administered by inoculation into or onto the mucous membranes of the subject animal. For example, the vaccine may be administered urethrally or genitally as a liquid or in the form of a pessary. In another embodiment, it may be administered to the mucosa of the lungs as a spray or vapor suspension.

Since at least thee amino acids are required to produce an antigenic epitope, the vaccine should comprise at least three consecutive amino acids, preferably at least five consecutive amino acids, and may comprise at least 10, 15, 25, 30, 40, or 45 consecutive amino acids of the infection-specific proteins as shown in SEQ ID NOS: 2, 4, 6, 8, 10, 12, 14, 16, and 18.

The vaccine of the invention may be used to inoculate potential animal targets of any of the chlamydial diseases including those caused by *C. psittaci. C. trachomatis, C. pneumoniae* or *C. pecorum*. Indeed the vaccine of the invention may be used to inoculate animals against any disease that shows immunological cross-protection as a result of exposure to infection-specific Chlamydia antigen.

Vaccines of the present invention can include effective amounts of immunological adjuvants known to enhance an immune response (e.g., alum). The protein or polypeptide is present in the vaccine in an amount sufficient to induce a protective immune response whether through humoral or cell mediated pathways or through both. Such a response protects the immunized animal against chlamydial infections specifically by raising an immune response against the Reticulate Body form of Chlamydia. Protective antibodies may be elicited by a series of two or three doses of the antigenic vaccine given about two weeks apart.

The present invention also teaches a method of making a vaccine against chlamydial infections. The method of making the vaccine comprises providing a pure (or substantially pure) infection-specific chlamydial peptide or portion thereof, and mixing the peptide with a pharmacologically acceptable excipient or adjuvant. Adjuvants may include commonly used compounds such as alum. Additionally, the vaccines may be formulated using a peptide according to the present invention together with a pharmaceutically acceptable excipient such as water, saline, dextrose and glycerol. The vaccines may also include auxiliary substances such as emulsifying agents and pH buffers. Doses of the vaccine administered will vary depending on the antigenicity of the particular peptide or peptide combination employed in the vaccine and characteristics of the animal or human patient to be vaccinated.

The infection-specific vaccine of the invention is directed towards not only *C. psittaci*, but against all forms of Chlamydia including *C. pneumoniae, C. trachomatis* and *C. pecorum*, and the vaccine may comprise not just peptides derived from *C. psittaci*, but also orthologous peptides and fragments of such orthologous peptides from other species of Chlamydia and peptides that are substantially similar to such peptides.

The present invention also teaches a method of vaccination comprising administering a vaccine formulated as described above to an animal either intravenously, intramuscularly, subcutaneously, by inhalation of a vapor or mist, or by inoculation in the form of a liquid, spray, ointment, pessary or pill into or onto the mucous membranes of the mouth, nose, lungs or urogenital tract or colon.

The methods of the invention may be practiced equally with human or non-human animal subjects.

The present invention also teaches a method of detecting Chlamydia infection-specific proteins produced by the Reticulate Body form of the organism. In this embodiment, antibodies raised to the infection-specific proteins are used in an immunological assay such as an Enzyme Linked Immunosorbant Assay or Biotin-Avidin assay or a radioimmunoassay or any other assay wherein specific antibodies are used to recognize a specific protein. Such assays may be used to detect both the quantity of proteins present and also the specificity of binding of such proteins. In such an assay, antibodies have attached to them, usually at the Fc portion, a detectable label, such as an enzyme, fluorescent marker, a radioactive marker or a Biotin-Avidin system marker that allows detection. A biological sample is provided from an animal that has been putatively exposed to Chlamydia. Such a sample may be, for example, whole blood, serum, tissue, saliva or a mucosal secretion. The sample is then contacted with the labeled antibody and specific binding, if any, is detected. Other methods of using infection-specific antibodies to detect infection-specific antigens that are present in cells or tissues include immunofluorescense, indirect-immunofluorescense and inmmunohistochemistry. In immunofluorescense, a fluorescent dye is bound directly to the antibody. In indirect-immunofluorescence, the dye is bound to an anti-immunoglobulin. Specific binding occurs between antigen and bound antibody is detected by virtue of flourescent emissions from the dye moiety. This technique would be particularly useful, for instance, for detection of Chlamydia antigen present on a urogenital mucosal smear.

Other techniques, such as competitive inhibition assays may also be used to assay for antigen, and one of ordinary skill in the art will readily appreciate that the precise methods disclosed may be modified or varied without departing from the subject or spirit of the invention taught herein.

The present invention also teaches a method of detection of Chlamydia infection-specific antibodies made against the Reticulate Body. In this embodiment a sample is provided from an animal putatively exposed to Chlamydia to determine whether the sample contains infection-specific antibodies. Such a sample may be, for example, whole blood, serum, tissue, saliva or a mucosal secretion. This sample is contacted with infection-specific antigens such that the amount and specificity of binding of the antibody may be measured by its binding to a specific antigen. Many techniques are commonly known in the art for the detection and quantification of antigen. Most commonly, the purified antigen will be bound to a substrate, the antibody of the sample will bind via its Fab portion to this antigen, the substrate will then be washed and a second, labeled antibody will then be added which will bind to the Fc portion of the antibody that is the subject of the assay. The second, labeled antibody will be species specific, i.e., if the serum is from a human, the second, labeled antibody will be anti-human-IgG antibody. The specimen will then be washed and the amount of the second, labeled antibody that has been bound will be detected and quantified by standard methods.

The present invention also teaches a method of treating a Chlamydial infection by directing a therapeutic agent against a specific target, such as: (i) an infection-specific protein of Chlamydia, (ii) a gene that encodes an infection-specific protein of Chlamydia and (iii) an RNA transcript that encodes an infection-specific protein of Chlamydia, wherein said therapeutic agent interacts with said target to affect a reduction in pathology.

For example, the present invention teaches a method of treating chlamydial infection wherein antisense technology is used to prevent the expression of infection-specific genes, thereby preventing the pathologies associated these proteins and preventing reproduction of the RB phase of Chlamydia. In this embodiment, RNA molecules complementary to transcripts of infection specific genes are introduced into the host cells that contain Chlamydia, and by binding to the mRNA transcripts of the infection-specific genes, prevent translation and therefore expression of the infection-specific proteins that are associated with pathogenesis.

The invention may be practiced to produce a vaccine against any species of Chlamydia, including *C. psittaci, C. pecorum, C. trachomatis* and *C. pneumoniae.*

The following examples illustrate various embodiments of the invention.

EXAMPLE 1

Homologous Sequences

The DNA and protein sequences discussed herein are shown in SEQ ID NOS:1–18. These sequences refer to infection-specific proteins and to the DNA sequences that encode these proteins. Although these sequences are from *C. psittaci* and *C. trachomatis*, it would be equally possible to substitute in the present invention, the orthologs of these sequences from other Chlamydia species such as *C. pecorum* and *C. pneumoniae.*

Such orthologous sequences may be obtained from the appropriate organisms by isolation of the genome of the organism, digestion with restriction enzymes, separation of restriction fragments by electrophoresis and purification of these fragments and selection of fragments of appropriate size. Identity of the fragments can be confirmed by dot-blot and by standard DNA sequencing techniques. The orthologous sequences in different Chlamydia species may also be found by selection of appropriate PCR primers (selected from appropriate regions flanking the Chlamydia gene of interest), and tie use of these primers in a PCR reaction, using the genome of the particular species of Chlamydia of interest as a template, to amplify the ortholog of interest. Such PCR primers would be selected from the flanking regions to allow specific amplification of the target gene. The fragments so obtained could then be run on a gel to check size and sequenced and compared against the known sequences to determine sequence identity.

The degree of sequence identity between the infection-specific genes of *C. psittaci* or *C. trachomatis* and their orthologs from *C. pecorum* and *C. pneumoniae*, may be determined by comparing sequences using the National Center for Biotechnology Information (NCBI) Basic Local Alignment Search Tool (BLAST) as described herein.

Orthologues of interest infection-specific proteins are characterized by possession of at least 50% or greater sequence identity counted over the full length alignment with one of the disclosed amino acid sequences of the *C. psittaci* or *C. trachomatis* infection-specific proteins using gapped blastp set to default parameters (described herein).

EXAMPLE 2

Heterologous Expression or Infection-specific Antigens

Methods for expressing large amounts of protein from a cloned gene introduced into *Escherichia coli* (*E. coli*) may be utilized for the purification of the Chlamydia peptides. Methods and plasmid vectors for producing fusion proteins and intact native proteins in bacteria are well known and are described in Sambrook et al. (1989). Such fusion proteins may be made in large amounts, are relatively simple to purify, and can be used to produce antibodies. Native proteins can be produced in bacteria by placing a strong, regulated promoter and an efficient ribosome binding site upstream of the cloned gene. If low levels of protein are produced, additional steps may be taken to increase protein production; if high levels of protein are produced, purification is relatively easy.

Often, proteins expressed at high levels are found in insoluble inclusion bodies. Methods for extracting proteins from these aggregates are described in chapter 17 of Sambrook et al. (1989). Vector systems suitable for the expression of lacZ fusion genes include the pUC series of vectors (Ruther et al. (1983)), pEX1–3 (Stanley and Luzio (1984)) and pMR100 (Gray et al. (1982)). Vectors suitable for the production of intact native proteins include pKC30 (Shimatake and Rosenberg (1981)), pKK177-3 (Amann and Brosius (1985)) and pET-3 (Studiar and Moffatt (1986)).

Fusion proteins may be isolated from protein gels, lyophilized, ground into a powder and used as antigen preparations.

Mammalian or other eukaryotic host cells, such as those of yeast, filamentous fungi, plant, insect, amphibian or avian species, may also be used for protein expression, as is well known in the art. Examples of commonly used mammalian host cell lines are VERO and HeLa cells, Chinese hamster ovary (CHO) cells, and WI38, BHK, and COS cell lines, although it will be appreciated by the skilled practitioner that other prokaryotic and eukaryotic cells and cell lines may be appropriate for a variety of purposes, e.g., to provide higher expression, post-translational modification, desirable glycosylation patterns, or other features.

Additionally, peptides, particularly shorter peptides, may be chemically synthesized, avoiding the need for purification from cells or culture media. It is known that peptides as short as 3 amino acids can act as an antigenic determinant and stimulate an immune response. Such peptides may be administered as vaccines in ISCOMs (Immune Stimulatory Complexes) as described by Janeway & Travers, Immunobiology: The Immune System In Health and Disease, 13.21 (Garland Publishing, Inc. New York, 1997). Accordingly, one aspect of the present invention includes small peptides encoded by the nucleic acid molecules disclosed herein. Such peptides include at least 5, and may be at least 10, 15, 20, 25, or 30 or more contiguous amino acids of the polypeptide sequences described herein.

EXAMPLE 3

Production of Antibodies Specific for Infection-specific Antigens

Antibody against infection-specific antigen is encompassed by the present invention, particularly for the detection of Chlamydia infection-specific antigen. Such antibody may be produced by inoculation of an animal such as a guinea-pig or a monkey with infection-specific antigen produced as described above. Such antigen may be a polypeptide as disclosed herein, such as a complete or partial polypeptide from C. psittaci, C. trachoatis, C. pneumoniae or C. pecorum. As discussed above, any molecule that can elicit a specific, protective immune response may be used as a vaccine, but since a minimum of three amino acids are required to do this, a vaccine should comprise at least three amino acids.

The peptide for use in the vaccine of the invention may be naturally derived or may be synthetic such as those synthesized on a commercially available peptide synthesizer. The peptide may also comprise a complete or partial peptide derived from the *C. pneumoniae* or *C. pecorum* infection-specific orthologs of the *C. trachomatis* or *C. psittaci* proteins as set out herein.

In one method of production, a polygonal antibody is produced by providing a purified peptide which is diluted to 100 micrograms per milliliter in sterile saline and mixed with RiBi Trivalent Adjuvant (RiBi Immunochem Inc). The antigen/adjuvant emulsion is then administered to an anaesthetized guinea pig using a procedure as provided by the manufacturer. Serum is collected 14 days after secondary and tertiary immunizations.

Monoclonal antibody to epitopes of the Chlamydia peptides identified and isolated as described can be prepared from murine hybridomas according to the classical method of Kohler and Milstein (1975) or derivative methods thereof. Briefly, a mouse is repetitively inoculated with a few micrograms of the selected purified protein over a period of a few weeks. The mouse is then sacrificed, and the antibody-producing cells of the spleen isolated. The spleen cells are fused by means of polyethylene glycol with mouse myeloma cells, and the excess unfusedicells destroyed by growth of the system on selective media comprising aminopterin, e.g., Hypoxanthene, Aminopterin and Thymidine (HAT) medium. The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (1980). and derivative methods thereof. Selected positive clones can be expanded and their monoclonal antibody product harvested for use. Detailed procedures for monoclonal antibody production are described in Harlow and Lane (1988).

An alternative approach to raising antibodies against the Chlamydia peptides is to use synthetic peptides synthesized on a commercially available peptide synthesizer based upon the amino acid sequence of the peptides predicted from nucleotide sequence data.

In another embodiment of the present invention, monoclonal antibodies that recognize a specific Chlamydia peptide are produced. Optimally, monoclonal antibodies will be specific to each peptide, i.e., such antibodies recognize and bind one Chlamydia peptide and do not substantially recognize or bind to other proteins, including those found in uninfected human cells.

The determination that an antibody specifically detects a particular Chlamydia peptide is made by any one of a number of standard immunoassay methods; for instance, the western blotting technique (Sambrook et al., 1989). To determine that a given antibody preparation (for instance from a guinea pig) specifically detects one Chlamydia peptide by western blotting, total cellular protein is extracted from a sample of blood from an unexposed subject and from a sample of blood from an exposed subject. As a positive control, total cellular protein is also extracted from Chlamydia cells grown in vitro. These protein preparations are then electrophoreseds on a sodium dodecyl sulfate-polyacrylamide gel. Thereafter, the proteins are transferred to a membrane (for example, nitrocellulose) by western blotting, and the antibody preparation is incubated with the membrane. After washing the membrane to remove non-specifically bound antibodies, the presence of specifically bound antibodies is detected by the use of an anti-guinea pig antibody conjugated to an enzyme such as alkaline phosphatase; application of the substrate 5-bromo4-chloro-3-indolyl phosphate/nitro blue tetrazolium results in the production of a dense blue compound by immuno-localized alkaline phosphatase. Antibodies which specifically detect the Chlamydia protein will, by this technique, be shown to bind to the Chlamydia-extracted sample at a particular protein band (which will be localized at a given position on the gel determined by its molecular weight) and to the proteins extracted from the blood of the exposed subject. No significant binding will be detected to proteins from the unexposed subject.

EXAMPLE 4

Use of Infection-specific Sequences and Their Corresponding Peptides and Antibodies in Diagnostic Assays Another aspect of the present invention is a method for detecting the presence of anti-Chlamydia antibodies that react with infection-specific Chlamydia proteins, Chlamydia peptides and Chlamydia nucleic acid sequences in biological samples. These methods include detection of antigen and antibody by ELISA and similar techniques, the detection of proteins in a tissue sample by immunofluorescence and related techniques and the detection of specific DNA sequences by specific hybridization and amplification.

One aspect of the invention is an ELISA that detects anti-Chlamydia antibodies in a medical specimen. An immunostimulatory infection-specific Chlamydia peptide of the present invention is employed as an antigen and is preferably bound to a solid matrix such as a crosslinked dextran such as SEPHADEX (Pharmacia, Piscataway, N.J.), agarose, polystyrene, or the wells of a microtiter plate. The polypeptide is admixed with the specimen, such as blood, and the admixture is incubated for a sufficient time to allow antibodies present in the sample to immunoreact with the polypeptide. The presence of the positive immunoreaction is then determined using an ELISA assay, usually involving the use of an enzyme linked to an anti-immunoglobulin that catalyzes the conversion of a chromogenic substrate.

In one embodiment, the solid support to which the polypeptide is attached, is the wall of a microtiter assay plate. After attachment of the polypeptide, any nonspecific binding sites on the microtiter well walls are blocked with a protein such as bovine serum albumin. Excess bovine serum albumin is removed by rinsing and the medical specimen is admixed with the polypeptide in the microtiter wells. After a sufficient incubation time, the microtiter wells are rinsed to remove excess sample and then a solution of a second antibody, capable of detecting human antibodies is added to the wells. This second antibody is typically linked to an enzyme such as peroxidase, alkaline phosphatase or glucose oxidase. For example, the second antibody may be a peroxidase-labeled goat anti-human antibody. After further incubation, excess amounts of the second antibody are removed by rinsing and a solution containing a substrate for the enzyme label (such as hydrogen peroxide for the peroxidase enzyme) and a color-forming dye precursor, such as o-phenylenediamine is added. The combination of Chlamydia peptide (bound to the wall of the well), the human anti-Chlamydia antibodies (from the specimen), the enzyme-conjugated anti-human antibody and the color substrate will produce a color that can be read using an instrument that determines optical density, such as a spectrophotometer. These readings can be compared to a negative control such as a sample known to be free of anti-Chlamydia antibodies. Positive readings indicate the presence of anti-Chlamydia antibodies in the specimen, which in turn indicate a prior exposure of the patient to Chlamydia.

In another embodiment, antibodies that specifically recognize a Chlamydia peptide encoded by the nucleotide sequences disclosed herein are useful in diagnosing the presence of infection-specific Chlamydia antigens in a subject or sample. For example, detection of infection-specific antigens that are present in cells or tissues may be done by immunofluorescence, indirect-immunofluorescense and immunohistochemistry. In immunofluorescense, a fluorescent dye is bound directly to the antibody. In indirect-immunofluorescence, the dye is bound to an anti-immunoglobulin. Specific binding occurs between antigen and bound antibody is detected by virtue of fluorescent emissions from the dye moiety. This technique may be particularly useful, for instance, for detection of Chlamydia antigen present on a urogenital mucosal smear. Chlamydia may be present in urogenital mucosa, and a smear on a glass slide may be fixed and bathed in a solution containing an antibody specific to the infection-specific antigen. The slide is then washed to remove the unbound antibody, and a fluorescent anti-immunoglobulin antibody is added. The slide is washed again, and viewed microscopically under an appropriately wavelength of light to detect fluorescence. Fluorescence indicates the presence of Chlamydia antigen. Alternatively, a urogenital mucosal smear may be taken, the sample cultured with HeLa cells to produce large amounts of the RB form, and immunofluorescence may then be used to detect infection-specific Chlamydia antibodies.

Another aspect of the invention includes the use of nucleic acid primers to detect the presence of Chlamydia nucleic acids that encode infection-specific antigens in body samples and thus to diagnose infection. In other embodiments, these oligonucleotide primers will comprise at least 15 contiguous nucleotides of a DNA sequence as shown in SEQ ID NOS: 1, 3, 5, 7, 9, 11, 13, 15, or 17. In other embodiments, such oligonucleotides may comprise at least 20 or at least 25 or more contiguous nucleotides of the aforementioned sequences.

One skilled in the an will appreciate that PCR primers are not required to exactly match the target gene sequence to which they anneal. Therefore, in another embodiment, the oligonucleotides will comprise a sequence of at least 15 nucleotides and preferably at least 20 nucleotides, the oligonucleotide sequence being substantially similar to a DNA sequence set forth in SEQ ID NOS:1, 3, 5, 7, 9, 11, 13, 15, and 17. Such oligonucleotides may share at least about 75%, 85%. 90% or greater sequence identity.

The detection of specific nucleic acid sequences in a sample by polymerase chain reaction amplification (PCR) is discussed in detail in Innis et al., (1990). *PCR Protocols: A Guide to Methods and Applications*, Academic Press: San Diego, part 4 in particular. To detect Chlamydia sequences, primers based on the sequences disclosed herein would be synthesized, such that PCR amplification of a sample containing Chlamydia DNA would result in an amplified fragment of a predicted size. If necessary, the presence of this fragment following amplification of the sample nucleic acid could be detected by dot blot analysis. PCR amplification employing primers based on the sequences disclosed herein may also be employed to quantify the amounts of Chlamydia nucleic acid present in a particular sample (see chapters 8 and 9 of Innis et al., (1990)).

Alternatively, probes based on the nucleic acid sequences described herein may be labeled with suitable labels (such a $P^{32}$ or biotin) and used in hybridization assays to detect the presence of Chlamydia nucleic acid in provided samples.

Reverse-transcription PCR using these primers may also be utilized to detect the presence of Chlamydia RNA which is indicative of an ongoing infection.

EXAMPLE 5

Production of Chlamydia Vaccines

The purified peptides of the present invention may be used directly as immunogens for vaccination. Methods for using purified peptides as vaccines are well known in the art and are described in Yang et al. (1991), Andersen (1994) and Jardim et al. (1990). As is well known in the art, adjuvants such as alum, Complete Freund's Adjuvant (CFA) and Incomplete Freund's Adjuvant (IFA) may be used in formulations of purified peptides as vaccines. Accordingly, one embodiment of the present invention is a vaccine comprising one or more immunostimulatory C. trachomatis or C. psittaci peptides encoded by nucleotide sequences as shown in the attached sequence listing, together with a pharmaceutically acceptable adjuvant.

Additionally a vaccine may comprise a defined fraction of the disclosed peptide of C. trachomatis or C. psittaci or may comprise a peptide wherein the gene coding for the peptide shows substantial similarity to the DNA sequences disclosed herein, such as for orthologous genes of C. pneumoniae or C. pecorum.

Additionally, the vaccines may be formulated using a peptide according to the present invention together with a pharmaceutically acceptable excipient such as water, saline, dextrose and glycerol. The vaccines may also include auxiliary substances such as emulsifying agents and pH buffers.

It will be appreciated by one of skill in the art that vaccines formulated as described above may be administered in a number of ways including subcutaneous, intramuscular and intravenous injection. Doses of the vaccine administered will vary depending on the antigenicity of the particular peptide or peptide combination employed in the vaccine, and characteristics of the animal or human patient to be vaccinated. While the determination of individual doses will be within the skill of the administering physician, it is anticipated that doses of between 1 microgram and 1 milligram will be employed.

As with many vaccines, the vaccines of the present invention may routinely be administered several times over the course of a number of weeks to ensure that an effective immune response is triggered. Where such multiple doses are administered, they will normally be administered at from two to twelve week intervals, more usually from three to five week intervals. Periodic boosters at intervals of 1–5 years, usually three years, may be desirable to maintain the desired levels of protective immunity.

Alternatively, multiple immunostimulatory peptides may also be administered by expressing the nucleic acids encoding the peptides in a nonpathogenic microorganism, and using this transformed nonpathogenic microorganism as a vaccine.

Finally, a recent development in the field of vaccines is the direct injection of nucleic acid molecules encoding peptide antigens, as described in Janeway & Travers, (1997). Thus, plasmids which include nucleic acid molecules described herein, or which include nucleic acid sequences encoding peptides according to the present invention may be utilized in such DNA vaccination methods.

The vaccine of the invention may be used to inoculate potential animal targets of any of the chlamydial diseases including those caused by C. trachomatis, C. psittaci, C. pneumoniae or C. pecorum. Indeed the vaccine of the invention may be used to inoculate animals against any disease that shows immunological cross-protection as a result of exposure to infection-specific Chlamydia antigen. The protein or polypeptide is present in the vaccine in an amount sufficient to induce a protective immune response whether through humoral or cell mediated pathways or through both. Such a response protects the immunized animal against chlamydial infections specifically by raising an immune response against the Reticulate Body form of Chlamydia.

The above embodiments are set out only by way of example and are not intended to be exclusive, one skilled in the art will understand that the invention may be practiced in various additional ways without departing from the subject of the spirit of the invention.

REFERENCES

Akins, D. R., et al. (1997) *J. Bacteriol.* 179:5076–5086.
Amann and Brosius (1985). *Gene* 40:183.
Andersen (1994). *Infection & Immunity* 62:2536.
Ausubel et al. (1987). *Current Protocols in Molecular Biology*, ed. Greene Publishing and Wiley-Interscience: New York (with periodic updates).
Blanco, D. R., et al. (1995) *J. Bacteriol.* 177:3556–3562.
Bannantine, J. P., et al. (1997) *Abstr. Gen. Mtg. Amer. Soc. Microbiol.* D-004. Miami, Fla.
Bannanitne, J. P., et al. (1998) *Infect. Immun.* 66:6017–6021.
Blanco, D. R., et al. (1996) *J. Bacteriol.* 178:6685–6692.
Brown, W. J. and Farquhar, M. G. (1989) *Meth Cell Biol* 31:553–569.
Caldwell, H. D., et al. (1981) *Infect. Immunol.* 31:1161–1176.
Chou, P. Y. and Fasman, G. D. (1978) *Annu Rev Biochem* 47:251–276.
Engvall (1980). *Enzymol.* 70:419.
Gray et al. (1982). *Proc. Natl. Acad. Sci. USA* 79:6598.
Hackstadt, T., R. et al. (1992) *Infect. Immun.* 60:159–165.
Hardham, J. M., et al. (1977) *Gene* 197:47–64.
Harlow and Lane (1988). *Antibodies, A Laboratory Manual*, Cold Spring Harbor Laboratory, New York.
Innis et al. (1990) *PCR Protocols: A Guide to Methods and Applications*, Academic Press: San Diego.
Janeway & Travers (1997) *Immunobiology: The Immune System in Health and Disease* 13.21. Garland Publishing, Inc. New York.
Kohler and Milstein (1975) *Nature* 256:495.
Kyte, J. and Doolittle, R. F. (1982) *J Mol Biol* 157:105–132.
Peeling, R. and Burnham, R. (1996) *Emerging Infectious Diseases* 2 (4) 307–317.
Rockey, D. D., and Rosquist, J. L. (1994) *Infect Immun* 62:106–112.
Rockey, D. D., et al. (1995) *Mol Microbiol* 15:617–626.
Rockey, D. D., et al. (1996) *Infect Immun* 64:4269–4278.
Rockey, D. D., et al. (1997). *Mol Microbiol* 24:217–228.
Robson, B. and Suzuki, E. (1976) *J Mol Biol* 107:327–356.
Rockey, D. D., and Rosquist, J. L. (1994). *Infect Immun* 62:106–112.
Rockey, D. D., et al. (1995) *Mol. Microbiol.* 15:617–626.
Rockey. D. D., et al. (1997) *Mol. Microbiol.* 24:217–228.
Rothman, J. E., and F. T. Wieland (1996) *Science* 272:227–234.
Ruther and Muller-Hill (1983). *EMBO J.* 2:1791.
Sambrook et al. (1989) *Molecular Cloning: A Laboratory Manual*, 2nd ed., vol. 1–3, ed. Cold Spring Harbor Lab. Press: Cold Spring Harbor, N.Y.
Shimatake and Rosenberg (1981). *Nature* (London) 292:128.
Stanley and Luzio (1984). *EMBO J.* 3:1429.
Studiar and Moffatt (1986). *J. Mol. Biol.* 189:113.
Su, H., et al. (1990) *J. Exp. Med.* 172:203–212.
Yang et al. (1990) *J. Immunology* 145:2281–2285.
Yuan, Y., et al. (1992) *Infect Immun* 60: 2288–2296.

What is claimed is:

1. A composition for inducing an immune response in a subject, comprising two purified peptides wherein a first peptide comprises at least 10 contiguous amino acids of the amino acid sequence as set forth as SEQ ID NO: 8 and a second peptide comprises at least 10 contiguous amino acids of the amino acid sequence set, forth as SEQ ID NO: 14.

2. The composition of claim 1 wherein the first peptide comprises at least 15 contiguous amino acids of the amino acid sequence set forth as SEQ ID NO: 8 and the second peptide comprises at least 15 contiguous amino acids of the amino acid sequence set forth as SEQ ID NO: 14.

3. The composition of claim 1 wherein the first peptide comprises at least 20 contiguous amino acids of the amino acid sequence set forth as SEQ ID NO: 8 and the second peptide comprises at least 20 contiguous amino acids of the amino acid sequence set forth as SEQ ID NO: 14.

4. A composition for inducing an immune response comprising two purified peptides wherein the first peptide comprises the amino acid sequence as set forth as SEQ ID NO: 8 and the second peptide comprises the amino acid sequence set forth as SEQ ID NO: 14.

5. A method of making a composition for inducing an immune response in a mammal comprising combining a pharmaceutically acceptable excipient with two purified peptides wherein a first peptide comprises the amino acid sequence as set forth as SEQ ID NO: 8 and a second peptide comprises the amino acid sequence set forth as SEQ ID NO: 14.

6. A method of inducing an immune response in a subject, comprising administering a composition according to claim 1 to the subject, wherein the subject is a mammal.

7. A method of inducing an immune response in a subject, comprising administering a composition according to claim 3 to the subject, wherein the subject is a mammal.

8. The method of claim 5, wherein the mammal is a human.

9. The method of claim 6, wherein the mammal is a human.

10. A method of inducing an immune response in a subject, comprising administering a composition according to claim 2 to the subject, wherein the subject is a mammal.

11. The method of claim 10, wherein the mammal is a human.

12. The method of claim 7, wherein the mammal is a human.

13. A method of inducing an immune response in a subject, comprising administering a composition according to claim 4 to the subject, wherein the subject is a mammal.

14. The method of claim 13, wherein the mammal is a human.

15. The composition of claim 1 wherein the first peptide comprises at least 25 contiguous amino acids of the amino acid sequence set forth as SEQ ID NO: 8 and the second peptide comprises at least 25 contiguous amino acids of the amino acid sequence set forth as SEQ ID NO: 14.

16. A method of inducing an immune response in a subject, comprising administering a composition according to claim 15 to the subject, wherein the subject is a mammal.

17. The method of claim 16, wherein the mammal is a human.

18. The composition of claim 1 wherein the first peptide comprises at least 30 contiguous amino acids of the amino acid sequence set forth as SEQ ID NO: 8 and the second peptide comprises at least 30 contiguous amino acids of the amino acid sequence set forth as SEQ ID NO: 14.

19. A method of inducing an immune response in a subject, comprising administering a composition according to claim 18 to the subject, wherein the subject is a mammal.

20. The method of claim 19, wherein the mammal is a human.

21. The composition of claim 1 wherein the first peptide comprises at least 40 contiguous amino acids of the amino acid sequence set forth as SEQ ID NO: 8 and the second peptide comprises at least 40 contiguous amino acids of the amino acid sequence set forth as SEQ ID NO: 14.

22. A method of inducing an immune response in a subject, comprising administering a composition according to claim 21 to the subject, wherein the subject is a mammal.

23. The method of claim 22, wherein the mammal is a human.

24. The composition of claim 1 wherein the first peptide comprises at least 45 contiguous amino acids of the amino acid sequence set forth as SEQ ID NO: 8 and the second peptide comprises at least 45 contiguous amino acids of the amino acid sequence set forth as SEQ ID NO: 14.

25. A method of inducing an immune response in a subject, comprising administering a composition according to claim 24 to the subject, wherein the subject is a mammal.

26. The method of claim 25, wherein the mammal is a human.

27. A composition for inducing an immune response in a subject, comprising at least one purified peptide comprising at least 10 contiguous amino acids of the amino acid sequence set forth as SEQ ID NO: 14.

28. A method of inducing an immune response in a subject, comprising administering a composition according to claim 27 to the subject, wherein the subject is a mammal.

29. The method of claim 28, wherein the mammal is a human.

30. The composition of claim 27 wherein the sequence of the at least one peptide comprises at least 15 contiguous amino acids of the amino acid sequence set forth as SEQ ID NO: 14.

31. A method of inducing an immune response in a subject, comprising administering a composition according to claim 30 to the subject, wherein the subject is a mammal.

32. The method of claim 31, wherein the mammal is a human.

33. The composition of claim 27 wherein the sequence of the at least one peptide comprises at least 20 contiguous amino acids of the amino acid sequence set forth as SEQ ID NO: 14.

34. A method of inducing an immune response in a subject, comprising administering a composition according to claim 33 to the subject, wherein the subject is a mammal.

35. The method of claim 34, wherein the mammal is a human.

36. A method of making a composition for inducing an immune response in a mammal comprising combining a pharmaceutically acceptable excipient with at least one purified peptide comprising at least 10 contiguous amino acid residues of the amino acid sequence set forth as SEQ ID NO: 14.

37. A method of making a composition for inducing an immune response in a mammal, comprising combining a pharmaceutically acceptable excipient with a composition according to claim 1.

38. The method of claim 37, wherein the mammal is a human.

* * * * *